(12) United States Patent
Kwan

(10) Patent No.: US 7,207,800 B1
(45) Date of Patent: Apr. 24, 2007

(54) DENTAL IMPLANT SYSTEM AND ADDITIONAL METHODS OF ATTACHMENT

(76) Inventor: Norman Ho-Kwong Kwan, 209 Indian Valley Trail, Missisauga, Ontario (CA) L5G 2K5

( * ) Notice: Subject to any disclaimer, the term of this patent is extended or adjusted under 35 U.S.C. 154(b) by 636 days.

(21) Appl. No.: 10/195,007

(22) Filed: Jul. 12, 2002

Related U.S. Application Data

(63) Continuation-in-part of application No. 09/967,556, filed on Sep. 28, 2001, now abandoned.

(51) Int. Cl.
*A61C 8/00* (2006.01)
(52) U.S. Cl. .................................................. 433/173
(58) Field of Classification Search ................ 433/173, 433/172, 174, 175, 176
See application file for complete search history.

(56) References Cited

U.S. PATENT DOCUMENTS 5,564,921 A * 10/1996 Marlin ..................... 433/172
5,584,629 A * 12/1996 Bailey et al. ............... 411/178
6,139,585 A * 10/2000 Li ............................. 623/23.57

FOREIGN PATENT DOCUMENTS

WO   WO 02/45615 A1 *  6/2002

* cited by examiner

Primary Examiner—Melba N. Bumgarner
(74) Attorney, Agent, or Firm—Howard J. Greenwald; Peter J. Mikesell

(57) ABSTRACT

A dental implant assembly with an an abutment head integrally joined to an implant body. The top section of the abutment head a shape formed by a linear wall adjacent to an arcuate wall; a ledge is located beneath the top section of the abutment; and the abutment head extends above the ledge a distance of from about 2 to about 4 millimeters. The implant body has a base section and a neck section, each of which has a different degree of roughness.

21 Claims, 30 Drawing Sheets

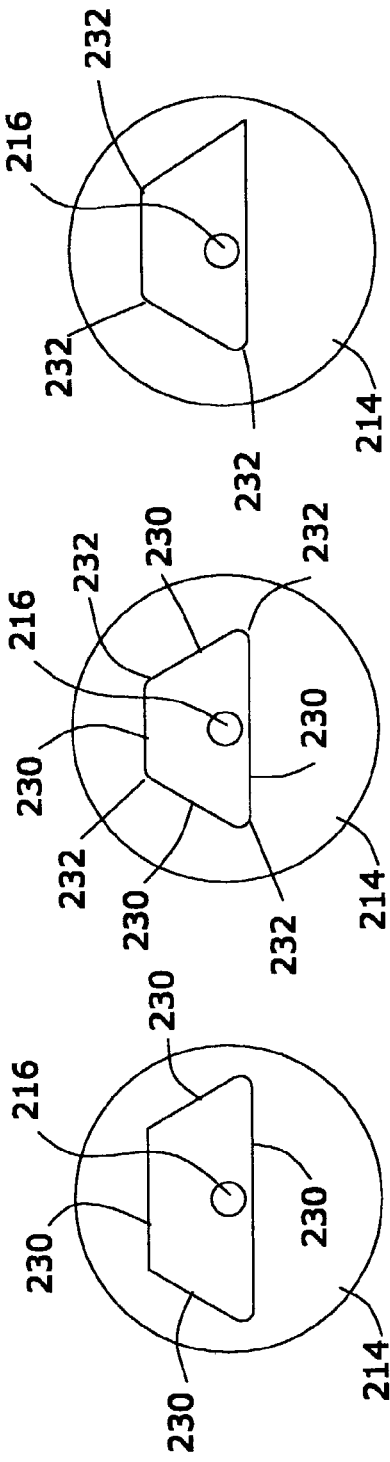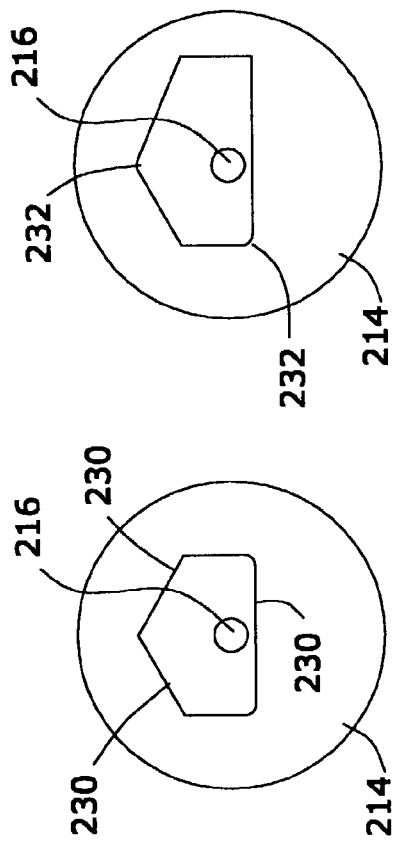

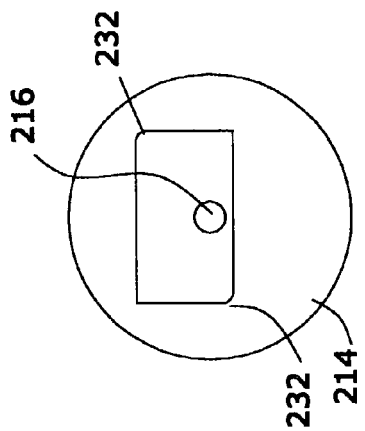
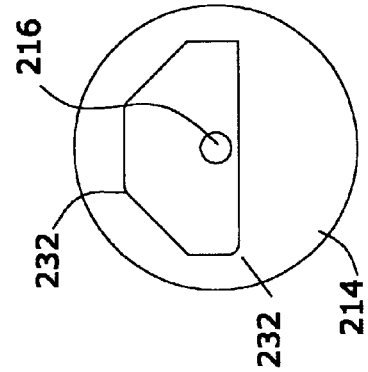
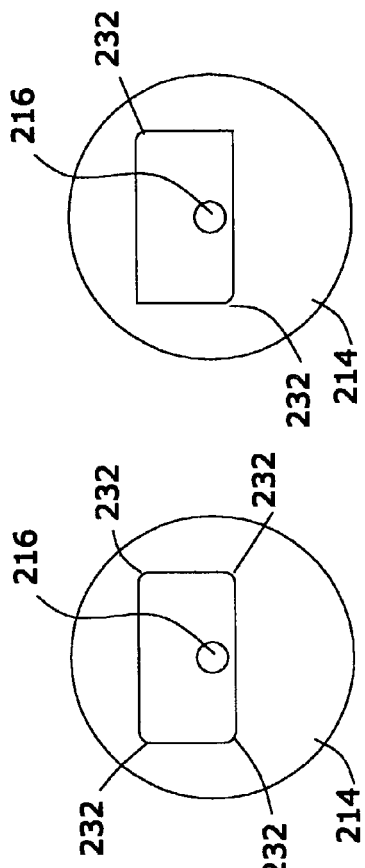
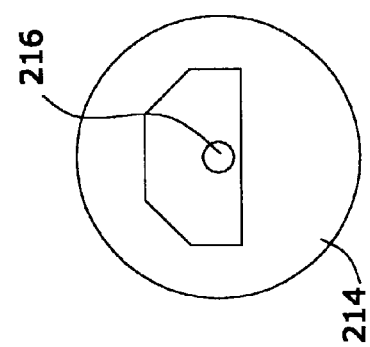
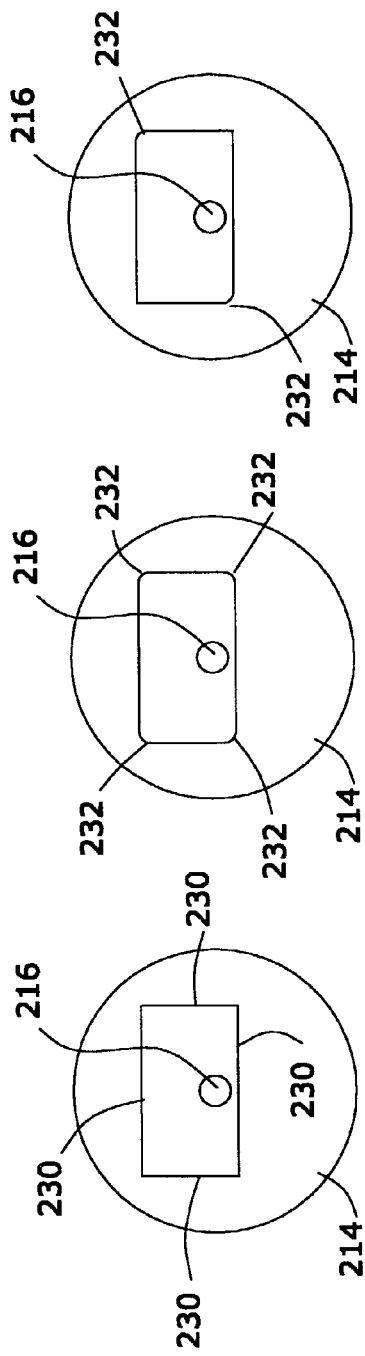
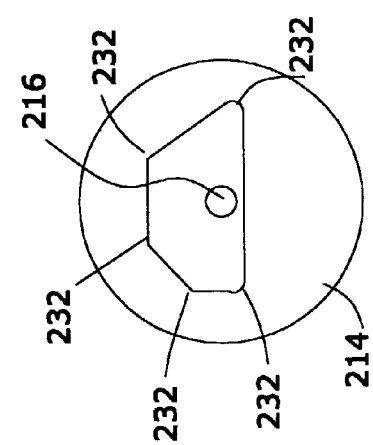

DENTAL IMPLANT SYSTEM AND ADDITIONAL METHODS OF ATTACHMENT

CROSS-REFERENCE TO RELATED PATENT APPLICATION

This application is a continuation-in-part of applicant's copending patent application U.S.S.N. 09/967,556, now abandoned, filed on Sep. 28, 2001.

FIELD OF THE INVENTION

A dental implant device comprised of an irregularly-shaped abutment.

BACKGROUND OF THE INVENTION

Dental implants have been known and used since at least the 1930's; see, e.g., U.S. Pat. No. 5,312,254 of Joel L. Rosenlicht. See also U.S. Pat. No. 5,145,371 of Lars Jomeus which discusses the osseointegration method of integrating a dental implant into a patient's jaw. The disclosure of each of these patents is hereby incorporated by reference into this specification.

A wide variety of dental implant styles and systems are currently available. For example, dental implants having cutting means are also known in the art, as disclosed in U.S. Pat. No. 5,338,197, the disclosure of which is hereby incorporated by reference into this specification. Another type of dental implant assembly is one that uses a hexagonal abutment implant system. This assembly is disclosed in U.S. Pat. No. 5,564,924, of which the disclosure is also herein incorporated by reference.

Applicant has described several dental implant devices in U.S. Pat. Nos. 5,574,924, 5,733,124, and 6,068,479; the entire disclosure of each of these United States patents is hereby incorporated by reference into this specification. Furthermore, reference also may be had to applicant's International Patent No. WO 02/26157 A1, the entire disclosure of which is also hereby incorporated by reference into this specification.

It is an object of this invention to provide an improved dental implant device.

SUMMARY OF THE INVENTION

In accordance with this invention, there is provided a universal dental implant system containing a head portion and a base portion. The base portion includes fastening elements to secure the implant within a jawbone of a patient. The head portion is comprised of a multiplicity of linear walls, at least one of which is disposed angularly in a manner different than the other such walls.

BRIEF DESCRIPTION OF THE DRAWINGS

The invention will be described by reference to the following drawings, in which like numerals refer to like elements, and in which:

FIGS. 30A, 30B, 30C, 30D, 30E, 30F, 30G, 30H, 30I, 30J, and 30K are top views of other preferred abutment assemblies;

DESCRIPTION OF THE PREFERRED EMBODIMENTS

Figure 1A:
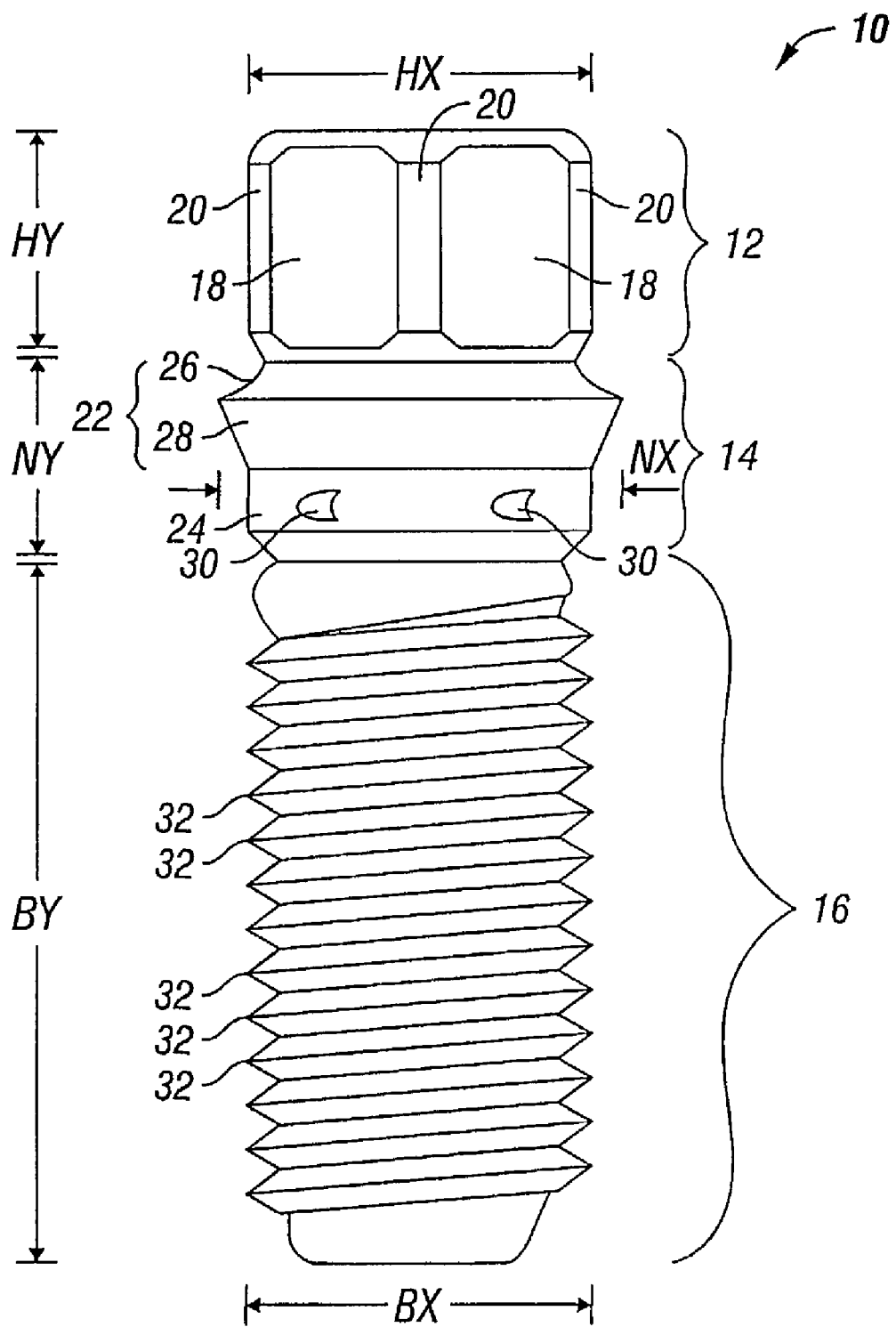
FIG. 1A is a schematic view of one preferred apparatus of the invention.

In general, dental implants are moderately expensive, ranging in cost from approximately two to four hundred dollars (excluding laboratory costs). However, the labor associated with the implant procedure often costs eight to twenty times the amount of the implant itself, ranging from about three to four thousand dollars per tooth. One of the reasons for this substantial cost is the multiplicity of steps required by the implant procedure. An example of these prior art steps will be described below with reference to Nobelpharma catalog PRI 385 94, 2nd edition (published by the Nobelpharma AB, Box 5190, S-402 26 Goteborg, Sweden).

In the first step of the prior art procedure, an implant or "fixture" is purchased; see, e.g., page 7 of the Nobelpharma catalog and the reference to the 3.75 millimeter and 4.0 millimeter titanium fixtures illustrated on such page. The fixture so purchased must then be placed into an "instrument set for fixture placement," which is shown on page 22 of the Nobelpharma catalog.

Once the fixture is disposed in the "instrument set . . . 2, "a "fixture mount" is then attached to the fixture by means of a wrench and a screwdriver. The "fixture mount" devices are shown on page 22 of the Nobelpharma catalog. The instruments for fixture placement of the fixture are also shown on page 22 of the Nobelpharma catalog (see wrench part 17 and screwdriver part 19).

Next, a "connection to contra-angle handpiece" (see part 11 on page 22 of the Nobelpharma catalog) is attached to a handpiece (see page 31 of the Nobelpharma catalog) and the implant assembly is then driven into the jawbone of a patient.

Thereafter, the fixture mount is removed from the fixture and a cover screw 10 (see page 9 of the Nobelpharma catalog) is inserted into the fixture. Next, the surgical site is allowed to heal for about three to about six months. See, e.g., Branemark/Zarb/Alberektsson: "Tissue Integrated Prostheses" (Quintessence Books, 1985).

After the healing period, the implant is exposed by surgical procedures and the cover screw is removed. A healing abutment (see page 39 of the Nobelpharma catalog) is then attached to the fixture. In general, the healing abutment is left in place for approximately two to three weeks, depending upon how the patient's tissue has healed.

Thereafter, the healing abutment is removed and an implant abutment is attached to the fixture. The type of implant abutment used will depend on the requirements of the patient. Thus, for example, referring to pages 38 and 39 of the Nobelpharma catalog, one may use a standard abutment, an "EsthetiConee" abutment, a "CeraOneo" abutment, a "Ball Attachment," an Angulated Abutment," and other standard and/or proprietary abutments.

Next, the desired prosthesis is formulated by conventional means and adjusted to fit within the patient's mouth. For a single-tooth prosthesis, generally one to two impressions are made to capture the size and shape of the abutment to the tooth.

Multiple mock-ups and adjustments are often made before the final prosthesis is finally secured to the implant.

For a multiple-tooth prosthesis, the course of treatment is not always predictable; multiple impressions and frameworks need to be created involving multiple appointments. Typically, the entire treatment, including initial implant placement and second stage surgery, would span a period of time ranging from two to approximately nine to eighteen months, or longer, before the final prosthesis is secured within the patient's mouth.

In addition to the increased time, labor and costs, various theoretical and practical implications need to be considered for multiple tooth or full-mouth reconstruction. In multiple restorations, "draw," "common path of insertion," "parallel," "passivity" and "stability' are terms that describe the most critical objectives of such a procedure.

Draw is perhaps best described as the effects of friction, but not binding.

Multiple implants and their abutments are rarely, if ever, perfectly aligned within the patient's mouth. Traditional methods of multiple tooth restoration require the heads/abutments and prostheses to be modified or made parallel until a common path of insertion is achieved and until the prosthesis is passive with respect to all of the abutments and soft tissue. In other words, it must be possible to place the prosthesis in position by moving the structure onto the abutments in a straight line (i.e., the common path of insertion), with sufficient friction or draw to ensure a firm fit. Once in place, the prosthesis must be passive, which means it must fit the abutments and the soft tissue profile such that there is no undue tension and no motion can take place.

These prior art procedures require a myriad number of instruments and parts, typically two surgical procedures, many trips by the patient to the dentist, increased treatment times and prolonged healing periods resulting in an overall reduced quality of life for the patient. Further, an expensive, time consuming and labor intensive "trial and error" system is crucial to such procedures because each prosthesis is custom made to the particular shape, design, location and quantity of abutments for each patient. Therefore, not only are the processes tedious and expensive, but, also, each surgical procedure introduces a certain element of risk, pain, and suffering.

In view of the above, there is a need for a dental implant system and associated process of attachment that are simple, predictable and effective. In particular, it is desirable that the dental implant system and attachment process include universal, interchangeable components, reduce post-operative infection, improve device/prosthesis strength and prolong its stability, and reduce the overall time for reconstruction procedures. It is also desirable that the dental implant system and associated process enable a practitioner to form a final prosthesis, including an infinite number of facsimiles of said final prosthesis, based on a single impression.

One embodiment of the present invention contemplates a method of dental reconstruction comprising inserting one or more devices into an edentulous space within a patient's mouth, wherein each of the devices includes a head portion. The method further includes placing a healing ball on each of the heads of the devices and forming a dental impression with impression material, wherein the healing balls transfer with the impression material upon removal from a patient's mouth. In addition, the method includes mounting an analog-abutment within each of the healing balls of the impression, forming a final model of the dental impression including the analog abutments, wherein the final model replicates the patient's edentulous space and creating a final prosthesis using the final model. Lastly, the method includes installing the final prosthesis within the edentulous space of the patient, The present invention also contemplate a universal dental implant system comprising a head portion and a base portion, wherein the base portion includes fastening elements to secure the implant within a jawbone of a patient. The system further includes a healing ball, wherein the healing ball mounts onto the head portion.

In addition, the system further includes a retaining screw or guide pin that secures the healing ball onto the head portion.

In addition, one embodiment of the present invention also contemplates a method of forming a dental prosthetic comprising fixing a stud element in a predetermined site, placing a removable protective element on the stud element and forming a first impression over the protective element at the predetermined site. The method also includes removing the protective element from the stud element with the first impression, mounting an abutment in the protective element contained in the first impression, forming a second impression over the abutment such that the second impression substantially replicates the predetermined site, and creating a prosthesis by relying on information provided by the second impression.

Another embodiment of the present invention contemplates a method of forming a dental prosthetic comprising providing a first impression which replicates a dental site, inserting a fixation element into the first impression, providing a second impression which replicates the dental site and retains the fixation element and modifying the fixation element on the second impression as needed so as to provide sufficient information to create the prosthetic.

Yet another embodiment of the present invention contemplates a model for creating a dental prosthetic comprising a form replicating the region of an edentulous space within a patient's mouth, the form having an analog abutment protruding from the region, and the analog abutment having a modification created to ensure insertability and removability of a prosthetic within a patient's mouth'.

FIG. 1A is a schematic illustration of one preferred implant system. Referring to FIG. 1A, an embodiment of a dental implant system in accordance with the present invention includes a one-piece universal implant abutment device 10. In general, the universal implant-abutment 10 is a single-piece device 10 including head 12, neck 14 and base 16 sections. It should be noted that this device 10 is a single-piece component.

However, it is to be understood that the disclosure of the present invention may also apply to devices including one or more elements. Further, the universal implant system of the present invention may be used to treat both humans and animals alike.

The implant-abutment device 10 shown in FIG. 1A is preferably made of titanium or titanium alloy. Alternatively, the device 10 may be made of one or more other materials including, but not limited to, metals and/or metal alloys, such as gold, silver, palladium, vanadium, cobalt alloy, stainless steel and the like, plastics, ceramics. Thus, by way of further illustration, one may use one or more of the materials disclosed in U.S. Pat. No. 61068,4792 U.S. Pat. No. 5,373,621, U.S. Pat. No. 5,372,660, U.S. Pat. No. 5,358,529, U.S. Pat. No. 5,354,390, U.S. Pat. No. 5,334,264, U.S. Pat. No. 5,326,362, U.S. Pat. No. 5,205,921, and U.S. Pat. No. 5,191,323, the disclosures of which are hereby incorporated by reference into this specification.

The device material should be biocompatible, nontoxic (e.g., medical grade) and provide sufficient strength and structural integrity when implanted within the jawbone of a patient.

Referring again to FIG. 1A, the height HY and diameter HX of the head 12 of the implant-abutment device are approximately within the range of 1.0 millimeter to about 8.0 millimeter, and 1.0 millimeer to 12.0 millimeters, respectively. In one embodiment of the invention, the height HY and diameter HX of the head are approximately 3.0 mm and 3.8 mm, respectively. The associated height NY and diameter NX of the neck 14 of the implant-abutment device 10 are approximately within the range of 0 millimeters to 8.0 millimeters and 1.0 millimeters to 12.0 millimeters, respectively.

In addition, the height BY and diameter BX of the base 16 of the device 10 are within the range of approximately 6.0 mm to 30.0 mm and 1.0 mm to 12.0 mm, respectively.

Alternative heights and diameters can also be used provided that the overall device dimensions permit proper implantation and functioning of the device 10.

Figure 1B:
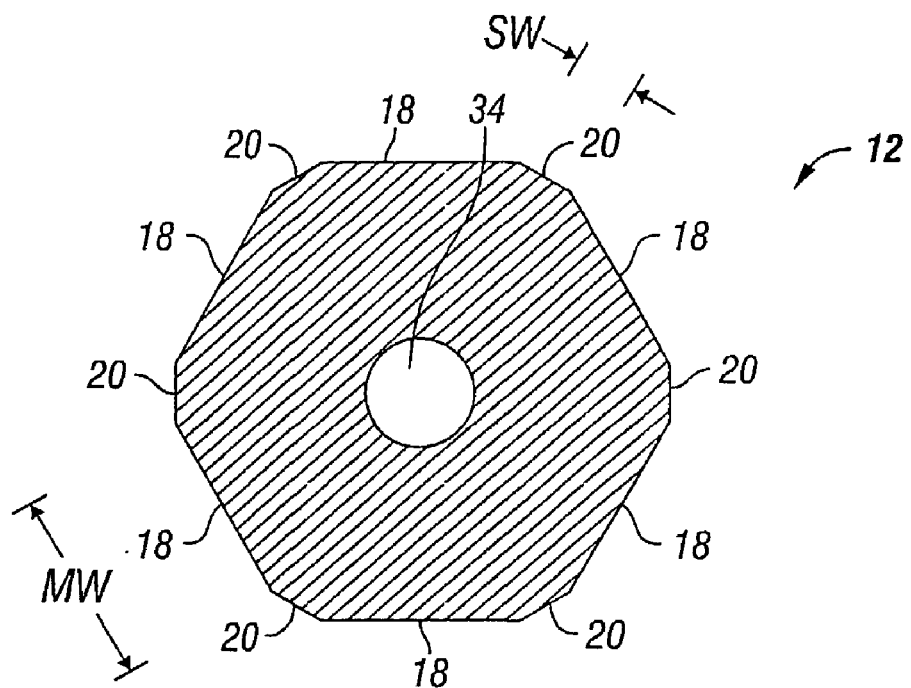
FIGS. 1B is a top view of another embodiment of the invention.

As shown in FIGS. 1A and 1B, and in the preferred embodiment depicted therein, the perimeter of the head 12 is substantially in the shape of a hexagon and includes six, planar, external main-walls 18. In one embodiment, the six, planar main-walls 18 are interconnected by six, substantially planar, external side-walls 20. In general, the width MW of each main-wall 18 is approximately within the range of 1.0 mm to 12.0 mm and the width SW of each sidewall 20 is approximately within the range of 0 mm to 12.0 mm, In another embodiment of the invention, the head configuration includes substantially planar main-walls 18 an d non-planar (e.g., arcuate) side-walls 20, thereby producing improved comfort and reduced irritation within the patient's mouth.

Alternatively, the main walls 18 may be substantially non-planar and the side walls 20 planar, or both the main walls 18 and side walls may be substantially non-planar.

Figure 2:
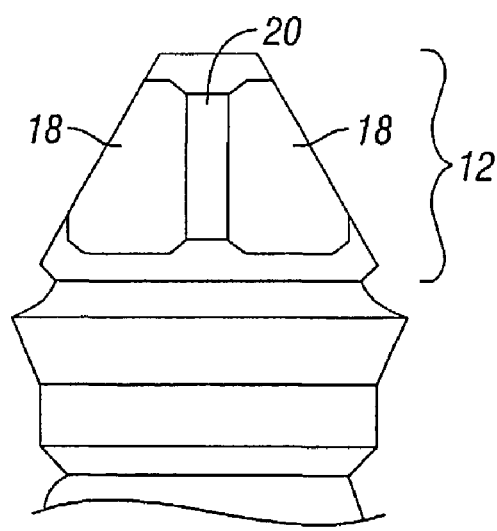
FIG. 2 is a partial side view of one preferred one-piece universal implant-abutment device.

In an alternate embodiment, shown in FIG. 2, the walls 18,20 of the head 12 are tapered. The walls 18,20, or portions thereof, may taper in either radially inward or outward direction. Other configurations of the head 12 including, but not limited to, cylindrical, triangular, square, and octagonal-shaped are also included within the scope of the claimed invention. Additional shapes, such as those disclosed in U.S. Pat. No. 6,068,479, of which the entire disclosure is incorporated by reference 8, the configuration of the base 16 and threads 32 includes, but is not limited to, those configurations as disclosed in U.S. Pat. No. 5,338,197, U.S. Pat. No. 5,435,723, U.S. Pat. No. 5,564,924, U.S. Pat. No. 5,571,017, U.S. Pat. No. 5,601,429, U.S. Pat. No. 5,967,783 and U.S. Pat. No. 6,068,479; the disclosure of each of these patents is hereby incorporated by reference into this specification. The threads 32 serve to securely attach the base 16 of the implant-abutment device 10 within the patient's jaw. Other fastening elements including, but not limited to, barbs, retractable barbs, one-way barbs and other textured surfaces may also be used with the present invention.

The cylindrical base 16 of the device 10 may be solid or partially hollow. The structural design of the base 16 depends, in part, on the material or materials used to fabricate the device 10. For example, in one embodiment, a base 16 made of a semirigid material may be solid, whereas a base 16 made of a substantially rigid material may be partially hollow. Alternatively, a base 16 made of a combination of rigid and 5 semi-rigid materials may include solid and hollow portions. Alternate configurations of the base 16 not disclosed herein are also included within the scope of the claimed invention.

Figure 3:
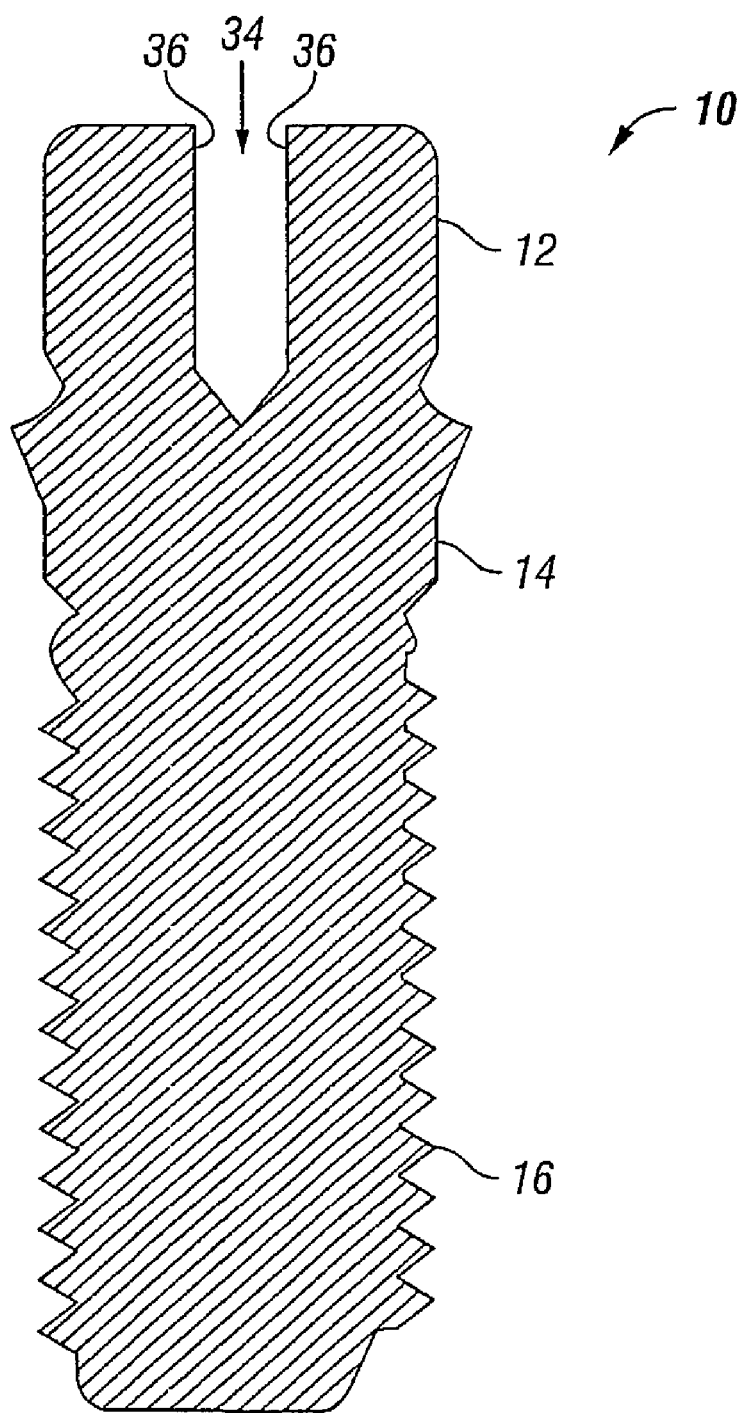
FIG. 3 is a sectional view of the device of FIG. 1A.

Referring to FIG. 3, a substantially cylindrical, hollow core 34 extends through and along the axial length, or portions thereof, of the head 12 of the device 10. The surface of the internal walls 36 of the head 12 surrounding the core 34 may be threaded and slightly tapered. Alternative core 34 and surrounding wall/wall-surface designs and configurations including smooth, dimpled, grooved, hexagonal, polygonal, tapered, stepped, arcuate and other configurations and combinations thereof, may also be used and are also included within the scope of the claimed invention. In one embodiment, the hollow core 34 is adapted to receive and securely retain a guide pin, retaining screw and/or healing ball, as described in further detail below.

In alternate embodiments (not shown), the hollow core 34 extends through and along the axial length, or portions thereof, of the head 12 and neck 14, or head 12, neck 14 and base 16. In yet another embodiment, the hollow-core 34 may be off-axis and/or non-parallel to the axial length of the device 10.

Figure 4:
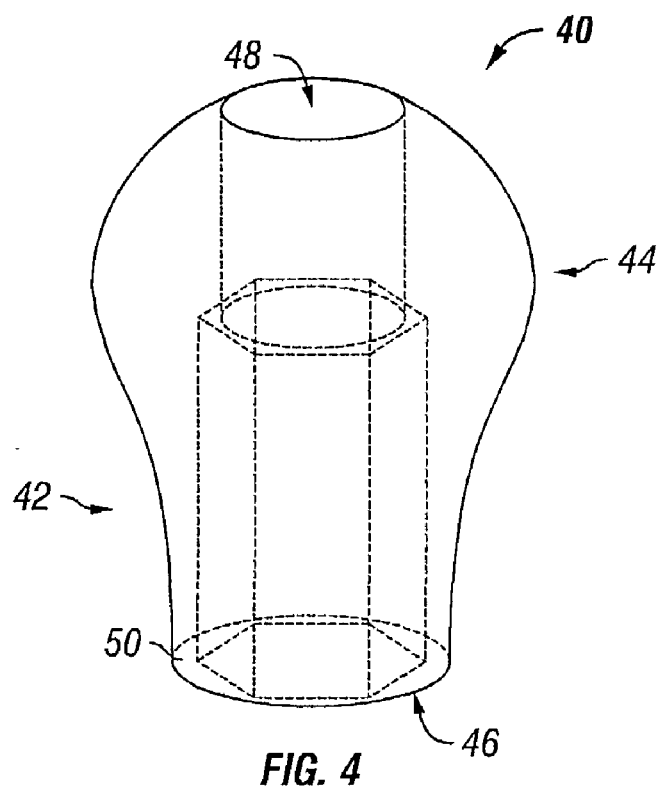
FIG. 4 is a schematic view of a healing ball of a preferred dental implant system.

The dental implant system of the present invention may also include a healing ball 40, shown in FIG. 4, that can be either removably secured or permanently affixed to the universal implant-abutment device 10. The healing ball 40 may be made of a variety of materials and combination of materials including, but not limited to, medical grade polyethylene, high-density polyethylene, K-resin, plastics, ceramics, metals and metal-alloys. In general, the healing ball 40 may be made of any biocompatible, non-toxic (e.g., medical grade) material that permits proper functioning of the healing ball 40. In another embodiment of the invention, the healing ball material may also include barium or similar elements that make the healing ball radiopaque.

Referring to FIG. 4, and in the preferred embodiment depicted therein, the healing ball 40 includes a cylindrical lower 42 portion and a spherical upper portion 44. Other healing ball configurations including, but not limited to, tooth-shaped, cone-shaped, box-shaped, donut-shaped, collar-shaped, cylindrical and spherical, may also be used with the dental implant system. In another embodiment (not shown), the healing ball 40 may include one or more small holes or recesses. These holes/recesses may function as gripping and/or anti-rotational/antitorquing features that are engaged when tightening, removing or repositioning the healing ball within the patient's mouth.

As shown in FIG. 4, and in the preferred embodiment depicted therein, a hexagonal-shaped bore or opening 46 extends along the axial length of the lower portion 42 and partially along the corresponding axial length of the upper portion 44. The hexagonal shape of the bore 46 is used for illustration purposes and not meant to limit the invention. In general, a variety of bore shapes or configurations adapted to engage the head 12 of the implant-abutment device 10 may be used with the healing ball 40 of the present invention.

In the embodiment depicted, a cylindrical bore or opening 48 lies adjacent to and is aligned along the same axis of the hexagonal bore 46. The diameter of the cylindrical opening 48 may be less than, equivalent to or greater than the diameter of the hexagonal bore 46. As will be described in further detail below, the cylindrical opening 48 forms a lumen through the healing ball 40, thereby enabling associated components, such as a guide pin, retaining screw, cement, wax and other components included within the scope 'of the claimed invention, to be inserted therethrough. In yet another embodiment (not shown), the opening 48 may be off-axis and/or non-parallel to the axis of the device 10.

Figure 5:
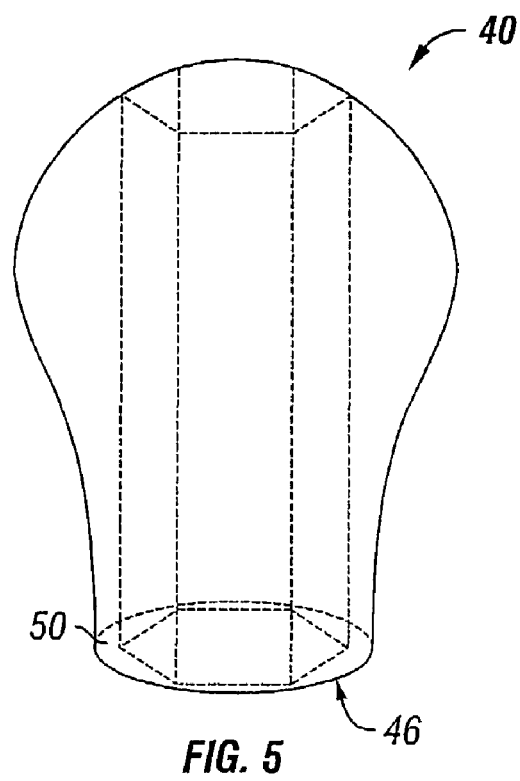
FIG. 5 is a schematic of another embodiment of a healing ball of the dental implant system.

In an alternate embodiment, shown in FIG. 5, the cylindrical bore 48 is removed and the hexagonal bore 46 forms the entire opening or lumen through the healing ball 40. In another embodiment (not shown), the hexagonal bore 46 is removed and the cylindrical bore 48 forms the entire opening or lumen through the 11 healing ball 40. For the sake of simplicity of representation, references to the opening 46 of the healing ball 40 in the remainder of this disclosure should be understood to include opening 46 and/or opening 48.

As previously described, the opening 46 of the healing ball 40 is configured to match and snugly fit over the hexagonal head 12 of the implant-abutment device 10. As such, an octagonal opening in a healing ball 40 would be used for a device 10 having an octagonal head 12, a triangular opening 46 in a healing ball 40 would be used for a device 10 with a triangular head 12, and so on.

In another embodiment (not shown), a reverse configuration of the manner in which the device 10 and healing ball 40 engage each other is contemplated. For example, the device 10 may include a recess, bore or opening into which the healing ball's 40 mating shaft, post or protrusion is inserted. Other methods of engagement not specifically disclosed herein but known in the art are also comprehended.

In an alternate embodiment (not shown), the opening 46 is formed of two opposing flat surfaces or walls and two opposing arcuate surfaces or walls. The two flat surfaces of the healing ball 40 engage two of the main-walls 18 of the implant/abutment head 12 and the two arcuate surfaces engage the remaining main-walls 18.

Thus, in the embodiment depicted, the healing ball 40 engages the device head 12 in a manner similar to a conventional wrench-and-socket configuration. Alternate embodiments of the opening 46 including, but not limited to, cylindrical, spherical, stepped, cylindrically-tapered, off-axis, non-parallel and other configurations not specifically disclosed herein, are also included within the scope of the claimed invention.

In another embodiment of the healing ball 40, the axial length of the opening 46 is approximately equivalent to the height HY of the head 12 (shown in FIG. 1).

Alternatively, the length of the opening 46 may be greater than the height HY of the head 12. In one embodiment, the base 50 of the healing ball 40 surrounding the opening 46 rests upon the ledge 26 of the device 10, ensuring a proper fit within the patient's mouth. In another embodiment (not shown), the opening of the healing ball 40 includes an inwardly-extending annular protuberance which is adapted to fit within and is removably secured to a matching annular groove surrounding the device 10.

This configuration and other embodiments disclosed in U.S. Pat. No. 6,068,479 (of which the specification is incorporated herein by reference) or not specifically disclosed herein are also included within the scope of the claimed invention.

The healing ball 40 is but one of many types of dental copings which may be used with the device 10 of the present invention. Other types of dental copings and/or gold cylinders including, but not limited to, those disclosed in U.S. Pat. No. 6,068,479, U.S. Pat. No. 5,733,124, U.S. Pat. No. 5,613,854, U.S. Pat. No. 51571,016, U.S. Pat. No. 51476, 383, U.S. Pat. No. 51439,380, U.S. Pat. No. 5,419,702, U.S. Pat. No. 51213,502, U.S. Pat. No. 51209,659, U.S. Pat. No. 5,145,371, U.S. Pat. No. 5,108,288, U.S. Pat. No. 5,040,983, U.S. Pat. No. 4,861,7672 U.S. Pat. No. 4,797,100, U.S. Pat. No. 4,698,0212 U.S. Pat. No. 47676,751, U.S. Pat. No. 4,492,579, U.S. Pat. No. 41459,112, U.S. Pat. No. 0.3;685, 114, RE 33,796, RE 33,272, RE 33,099, and the like may also be used with the implant-abutment device 10. The entire disclosure of each of these patents is hereby incorporated by reference into this specification.

In one embodiment of the present invention, the healing ball 40 may be removed from the implant-abutment device 10 prior to attachment of the dental prosthesis. As such, the healing ball 40 may serve as a temporary cover to protect the patient's tongue, inner-cheek and/or inner-lips from contacting potentially rough or abrasive edges of the device 10. In addition, the healing ball 40 may also function as a tissue spacer, as described in further detail below. Guide pins, retaining screws, wax or other attachment devices or compounds, including various combinations thereof, may be used to temporarily attach the healing ball 40 to the device 10. Once the final prosthesis is available, the attachment device or compound and healing ball are removed and the prosthesis is secured to the implant-abutment device 10 within the patient's mouth.

Figure 6A:
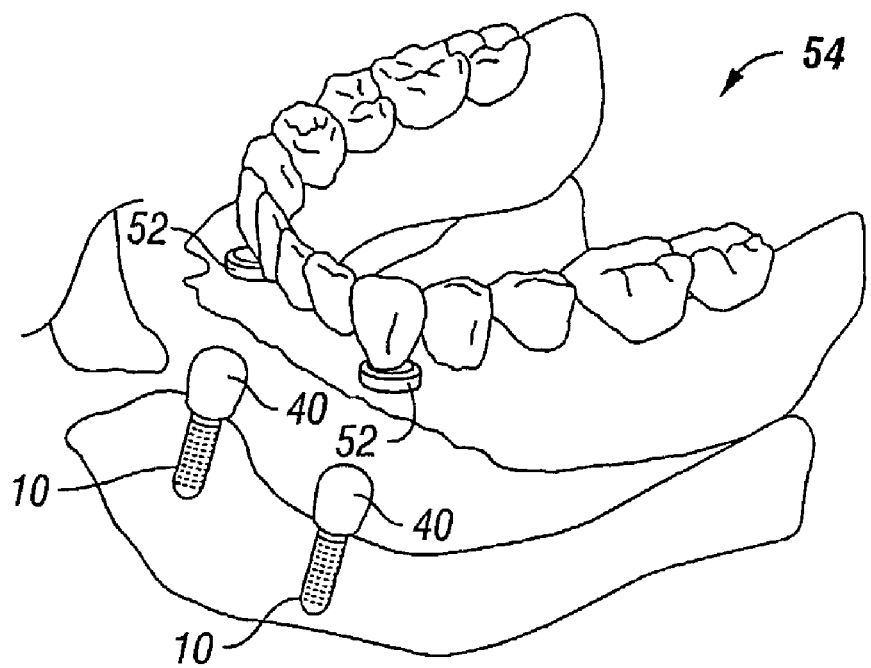
FIG. 6A is a perspective view of one embodiment of a dental implant system of the present invention as inserted within the jawbone of a patient.

In another embodiment of the invention, the healing ball 40 may be permanently affixed to the device 10 so that the dental prosthesis directly attaches to the healing ball 40. For example, prostheses or dentures including metal rings, caps with rubber o-rings, ball attachment replicas and other similar fastening elements may be friction fit over the healing ball 40 to firmly, securely and removably attach the prosthesis to the implant-abutment device 10. As shown in FIG. 6A, one or more healing ball 40 and implant-abutment device 10 assemblies are secured within the patient's mouth. Attachment devices and compounds including, but not limited to, cement, retaining screws, glues, wax, permanent soft-liner materials (such as, for example, silicone or Coe-softe) and other attachment devices and compounds, including combinations thereof, may be used to permanently secure the healing ball 13 onto the implant-abutment device 10. The fastening elements 52 of the prosthesis 54 are then friction fit over the healing balls 40 to securely attach the prosthesis 54 within the patient's mouth.

In an alternate embodiment, one or more tooth-shaped healing balls 40 are permanently affixed to one or more devices 10 implanted within the patient's jawbone.

Figure 6B:
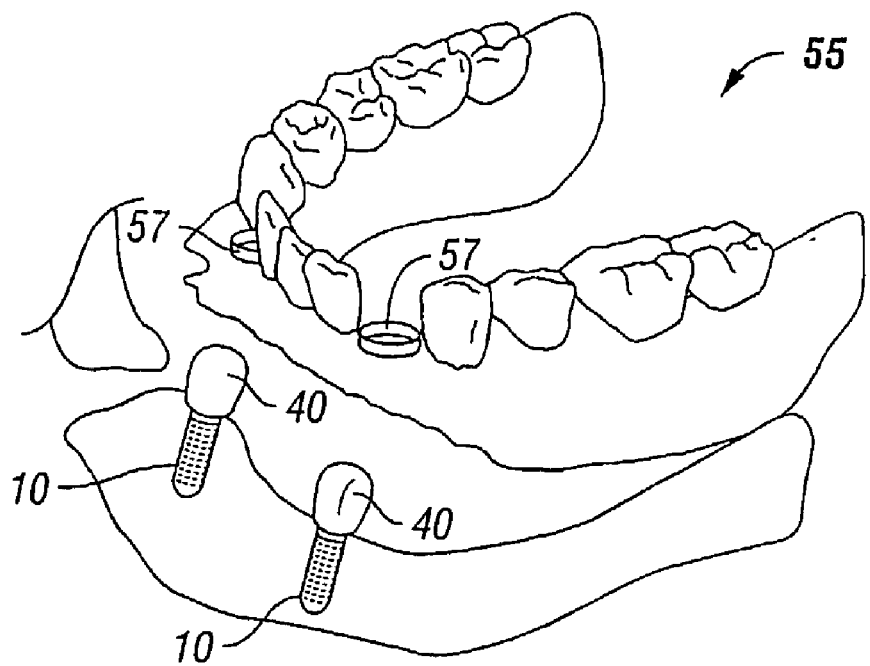
FIG. 6B is a perspective view of another embodiment of a dental implant system of the present invention as inserted within the jawbone of a patient.

As shown in FIGS. 6A and 6B, a prosthesis, denture or partial-denture 55 including one or more retention clasps, rings or elements 57 aligned to engage the healing ball(s) 40 act as retaining elements to secure and stabilize the denture in the patient's mouth.

Alternate configurations of attaching the dental implant system of the present invention either removably or permanently to a prosthesis well-known to those skilled in the art are also included within the scope of the present invention.

In another embodiment of the invention (not shown), bar-clip overdentures, crowns and/or bridges (such as those disclosed in U.S. Pat. No. 5,174,954, of which the entire disclosure is herein incorporated by reference) may be readily connected to either the healing ball 40 and implant-abutment device assemblies or to the gold-cylinder and implant-abutment device 10 assemblies. As will be apparent to those skilled in the art, the universality of the dental implant system of the present invention enables it to be used in conjunction with many different types of prosthetic applications. Further, it provides the dental practitioner with substantially more flexibility with reduced number of parts/components than the prior art systems.

Figure 7:
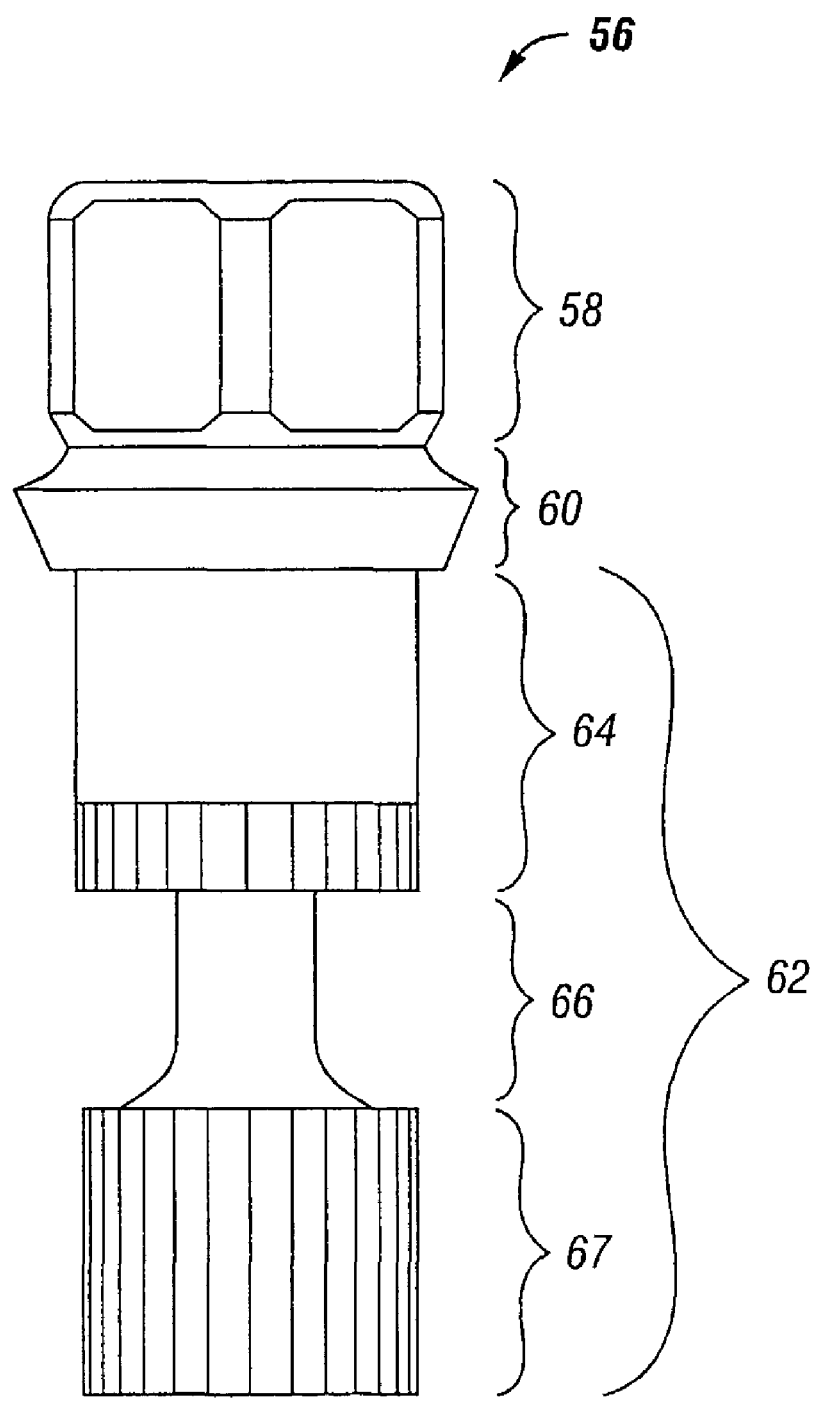
FIG. 7 is a schematic view of an analog-abutment of a dental implant system.

Referring to FIG. 7, the dental implant system may also include an abutment-analog 56. The abutment-analog 56 is generally a replica of the head 12 and/or neck 14 of the implant-abutment device 10 and mainly used in laboratory procedures during construction of patient models and prostheses. The abutment-analog includes a head 58 and neck 60 similar in design and configuration to the head 12 and neck 14 of the implant-abutment device 10 previously described.

In one embodiment, the head 58 and neck 60 of the abutment-analog 56 are exact replicas of the head 12 and neck 14 of the implant-abutment device 10.

The analog-abutment 56 may be made from a variety of materials. Examples of such materials include, but are not limited to, brass, gold, titanium, stainless steel, metals, metal-alloys, ceramics, plastics, composites and combinations thereof are also included within the scope of the claimed invention.

As shown in FIG. 7, the abutment-analog 56 also includes a shaft 62. In one embodiment, the shaft 62 includes cylindrically shaped top 64, middle 66 and bottom 14 portions. The diameter of each shaft portion 64, 66, 67 is variable, ranging in siz6 from approximately 1.0 mm to 10.0 mm. For example, in one embodiment the top portion 64 is approximately 3.0 mm, the middle portion 66 is approximately 1.75 mm and the bottom portion 67 is approximately 3.O mm. Alternatively, the top 64, middle 66 and bottom 67 portions maybe approximately 1.0 mm, 3.0 mm and 1.0 mm, respectively. In general, the shaft 62 may be configured with various gripping surfaces, projections, indentations, flat/planar portions and non-planar portions to prevent the analog-abutment 56 from becoming dislodged from or rotating around the rigid stone or plaster material that forms the final model for the prosthesis, as described in further detail below.

Figure 9:
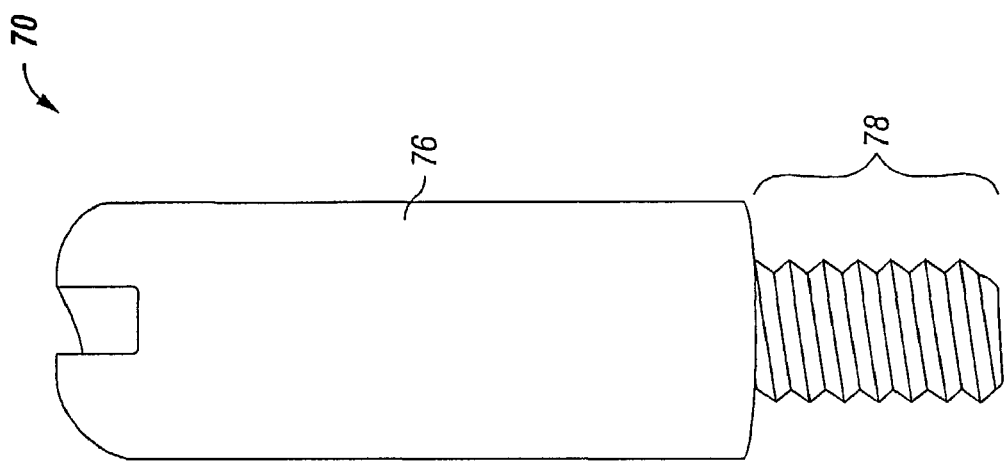
FIG. 9 is a perspective view of a guide pin of a dental implant system.
Figure 8:
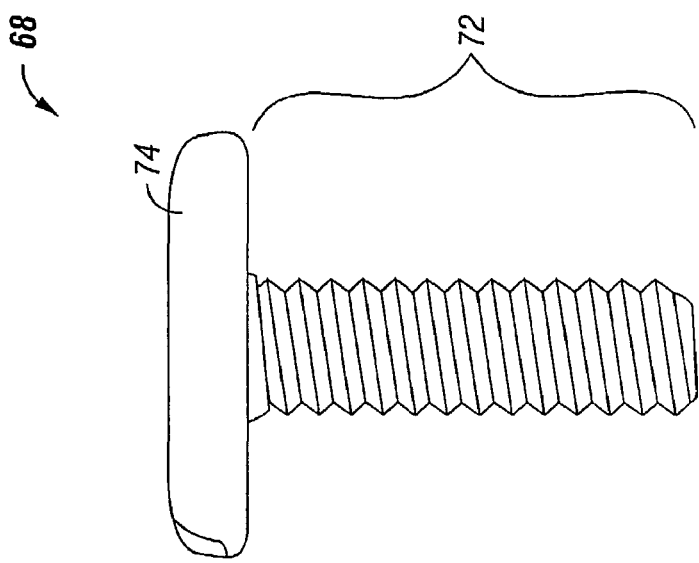
FIG. 8 is a perspective view of a retaining screw of a dental implant system.

Referring to FIGS. 8 and 9, the dental implant system of the present invention may also include a retaining screw 68 and guide pin 70, respectively. Referring to FIG. 8, the retaining screw 68 is used to secure the healing ball 40 and/or prosthesis, either permanently or temporarily, onto the implant-abutment device 10.

As such, the threaded portion 72 of the retaining screw 68 is configured to engage the threads on the surface of the internal walls 36 of the device 10. In general, the retaining screw may be approximately 2.0 mm to 10.0 mm in length. In one embodiment, the diameter of the head 74 of the retaining screw 68 may be configured to seat within the lumen of the healing ball 40. Alternatively, the head 74 may be seated on the external surface of the healing ball 40. The retaining screw 68 may be made of a variety of biocompatible, non-toxic materials including, but not limited to, brass, gold, titanium, stainless steel, metals, metal-alloys, ceramics, plastics, composites and combinations thereof.

The guide pin 70, shown in FIG. 9, is used to secure the healing ball 40 to the implant-abutment device 10 for taking final impressions of the position of the head 12 of the device 10. The length of the guide pin 70 is approximately within the range of 3.0 mm to 20.0 mm. In general, the guide pin 70 is configured so that a sufficient portion of the head or shaft 76 extends outside of the healing ball 40, enabling a user or practitioner to firmly and securely grip the guide pin 70. The shaft 76 may be made of a variety of shapes and surface configurations including, but not limited to, cylindrical, conical, polygonal, ribbed, dimpled, smooth and textured.

As with the retaining screw 68, the threaded portion 78 of the guide pin 70 may also be configured to engage the threads on the surface of the internal walls 36 of the device 10. In addition, a variety of biocompatible, non-toxic materials may be used to fabricate the guide pin 70 of the present invention. Examples of these materials include, but are not limited to, brass, gold, titanium, stainless steel,' metals, metal alloys, ceramics plastics, composites and combinations thereof are also included within the scope of the claimed invention.

Although the retaining screw 68 and guide pin 70 are shown in FIGS. 8 and 9, respectively, to include a slotted head, other head configurations known in the art to either manually or mechanically drive the screw 68/guide pin 70 into the device 10 may also be used and are included within the scope of the claimed invention. One or more of the universal implant-abutment device 10, healing ball 40, abutment-analog 56, guide pin 70 and retaining screw 68 components of the dental implant system of the present invention may be packaged together to form a kit (not shown). The size, material, shape and configuration of each component compliments the other components, thereby assuring compatibility, interchangeability, durability and perfect fit. In addition, component parameters, such as size, material, shape and configuration of each component for either single or multiple tooth replacement kits, may be the same or variable within each kit.

Each kit may be configured to provide the necessary components for a particular procedure. For example, in one embodiment of the invention, the kit for a single-tooth replacement procedure may include one implant abutment device 10, three healing balls 40, one analog abutment 56, one retaining screw 68 and one guide pin 70. In another embodiment, a single-tooth replacement kit may include two implant abutment devices 10, six healing balls 40, two analog abutments 56, two retaining screws 68 and two guide pins 70. In an alternate embodiment, a multiple-tooth replacement kit may include three implant abutment devices 10, nine healing balls 40, three analog abutments 56, three retaining screws 68 and three guide pins 70. Other kit configurations not disclosed herein but known in the art are also included within the scope of the claimed invention.

Many methods of using the universal implant system of the present invention are contemplated herein. Each methodology is related to the particular type of dental reconstruction required by the patient's condition. The following methods are intended as example and for illustration purposes only and are not meant to limit the claimed invention.

Figure 10:
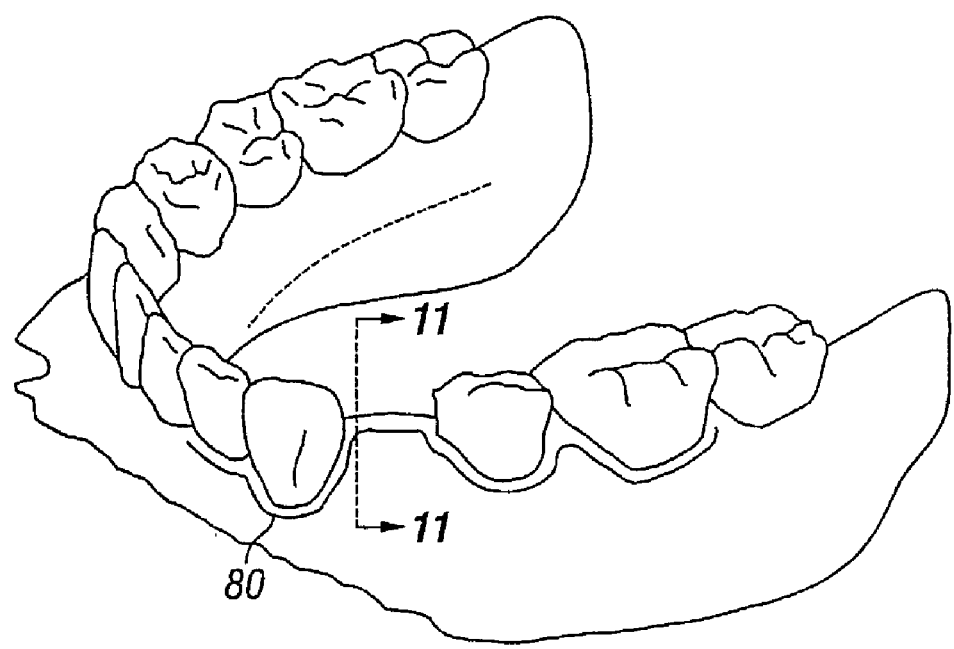
FIG. 10 is a schematic view of an incision formed as part of a process of attachment of the dental implant system in accordance with the present invention.
Figure 11:
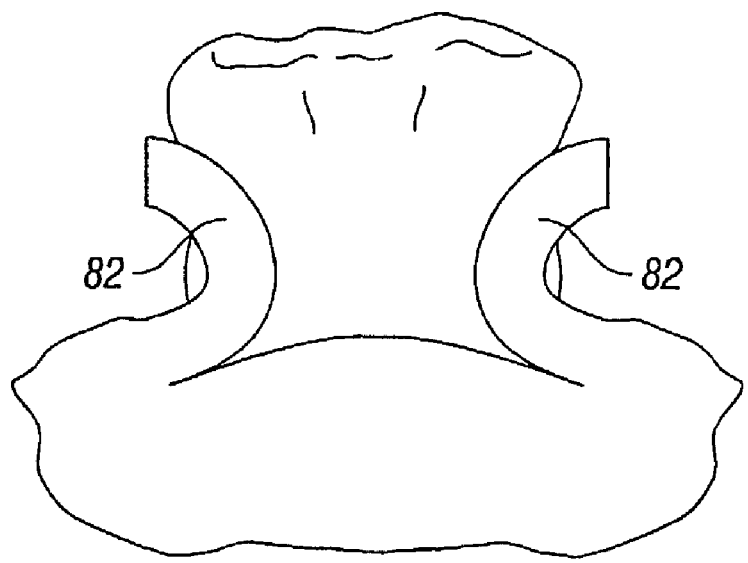
FIG. 11 is a schematic illustration of a tissue flap formed as part of the methods of attachment of a dental implant system.

In one embodiment, a mid-crestal and reverse bevel labial incision 80 is made extending along two teeth and on both sides of the edentulous space, as shown in FIG. 10. A similar incision is made palatally, resulting in —a full thickness envelope flap 82 as shown in FIG. 11.

Figure 12:
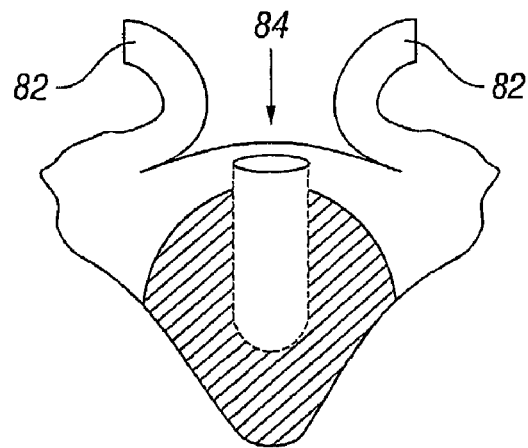
FIG. 12 is a schematic illustration of a hole formed as part of the methods of attachment of the dental implant system in accordance with the present invention.

Referring to FIG. 12, a hole 84 is then drilled within the jawbone of the patient. The exact point of purchase and approach, either cingulum or labial, within the edentulous space and jaw anatomy are visually determined. In general, the approach should be one that will provide the greatest amount of stability for the device 10, and, generally, is parallel to the long axis of adjacent teeth.

One or more drill bits used at variable speeds with sufficient irrigation create the appropriately sized and shaped hole 84. The depth of the hole 84 is sized to receive the base 16 of the implant-abutment device 10, and generally ranges from approximately 8 mm to 30 mm in depth.

Figure 13:
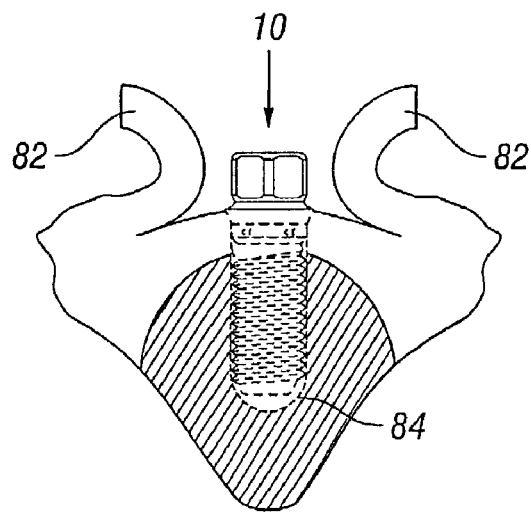
FIG. 13 is a schematic illustration of a implant-abutment device inserted within the hole of FIG. 12.

Referring to FIG. 13, the implant-abutment. device 10 is then manually inserted into the hole 84 in a sterile manner. In one embodiment, a carrier (not shown) may be used to deliver the implant-abutment device 10 to the hole 84 and also to begin manually screwing the device 10 into the hole 84. An example of such a carrier is disclosed in U.S. Pat. No. 6,068,479, of which the entire disclosure in incorporated herein by reference. Other carriers and similar tools not specifically disclosure herein but known in the art may also be used and are included within the scope of the claimed invention.

Generally, only a portion of the base 16 of the implant-abutment device 10 can be manually inserted into the hole 84. A power-driven socket-wrench, contra-angle handpiece or similar tool may be used to fully seat the device 10 within the hole 84.

Crestal bone height and clinical parameters such as device stability, tissue thickness as required for prosthesis aesthetics and inter-occlusal distance may also be taken into consideration to determine final position and configuration of the device 10.

The gingival tissue and flaps 82 are inspected, trimmed, coapted and sutured around the head 12 of the device 10. Factors, such as amount of tissue recession after healing, final crown space required and/or other aesthetic and prosthetic considerations, may be taken into account with respect to tissue placement and suturing.

Either immediately after suturing or anytime thereafter, the prosthesis may be attached to the device 10. No further surgical procedures are required, unlike prior art processes which often require a second stage surgery to expose and prepare a gingival seat around the device and perform other modifications to ensure proper prosthetic-device engagement. As previously described, with prior art devices and procedures, a space or recess between the device and. soft tissue must be created to allow an appropriate interface and ensure proper placement of the prosthesis without trapping soft tissue. In contrast, the prosthesis may be directly attached to the implant-abutment device 10 of the present invention without further surgical intervention.

Figure 14:
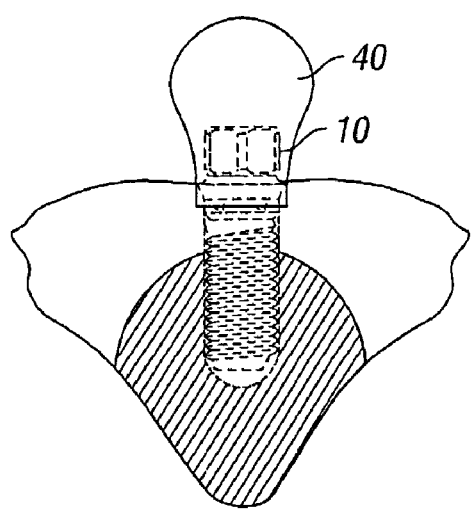
FIG. 14 is a schematic illustration of a healing ball seated on the device of FIG. 13.

Referring to FIG. 14, a healing ball 40 may be attached to the device 10 to contour the tissue for proper impression registration. In one embodiment of the invention, the healing ball 40 is attached directly after tissue suturing and prior to hard and soft tissue healing. A retaining screw 68 or similar component previously described may be used to secure the healing ball 40 onto the device 10. The healing ball 40 is then left in place for an approximately seven to ten day time period.

Alternate time periods that allow the soft tissue to mature and form a stable recess for the prosthesis may also be used.

After the soft tissue has matured and formed a stable recess, a final impression may be taken from which the prosthesis is created. The original healing ball 40 is removed, and another, interchangeable healing ball 40 is secured to the device 10 with a guide pin 70. Alternatively, the original healing ball 40 is left in place and the retaining screw 68 is replaced with a guide pin 70.

Figure 15:
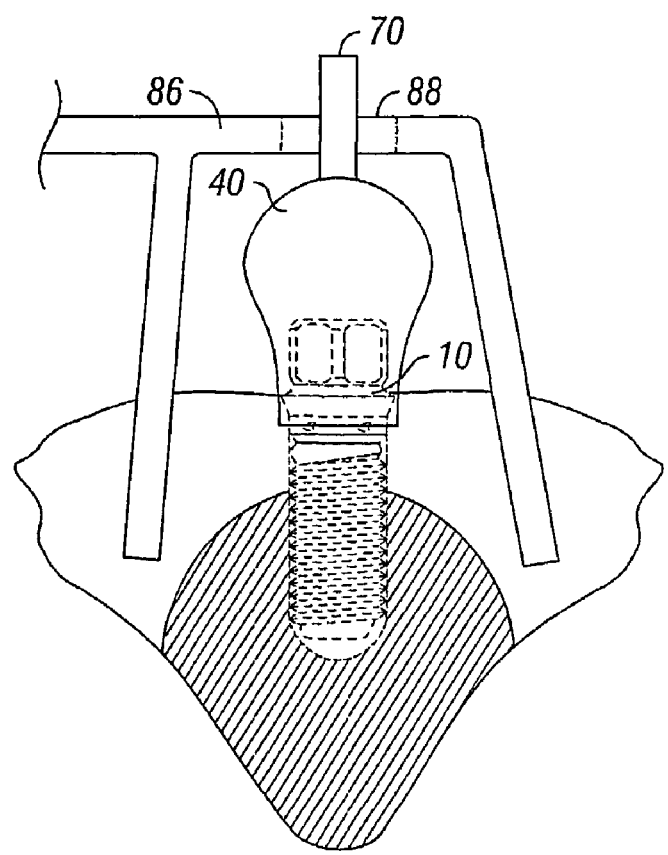
FIG. 15 is a schematic illustration of an impression tray.
Figure 16:
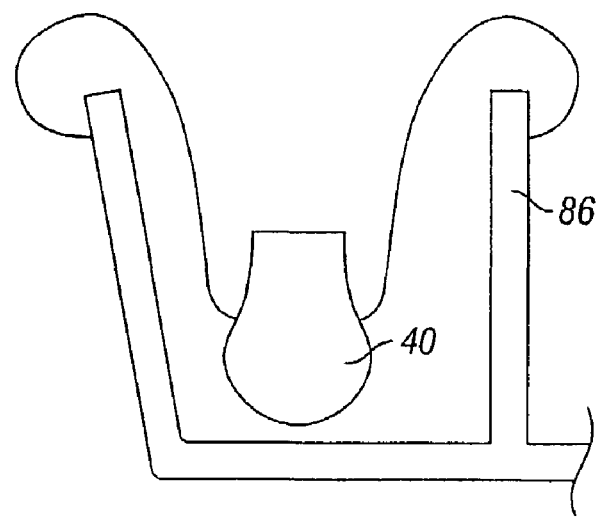
FIG. 16 is a schematic illustration of an impression formed as part of the process of attachment of a dental implant system.

As shown in FIG. 15, an impression tray 86 with a window or opening 88 is placed over the healing ball 40 within the patient's mouth. The opening 88 of the tray 86 is aligned with the guide pin 70 so that the guide pin 70 protrudes above the impression frame. The guide pin 70 holds the healing ball 40 in place during setting of the impression material. After the material is set, the protruding portion of the guide pin 70 is used to unscrew the guide pin 70 from the healing ball 40 and remove the guide pin 70 through the tray opening 88. The healing ball 40 is then transferred with the impression material when the impression tray 86 is removed from the patient's mouth, as shown in FIG. 16. The original healing bal-I 40 may be re-attached to the device 10 as a protective covering and tissue spacer.

In an alternate embodiment, anti-rotational grooves, indentations or other types of gripping features may be formed on the healing ball 40. These features prevent movement or displacement of the healing ball 40 within the impression material when the healing ball/impression tray are removed from the patient's mouth.

Figure 17:
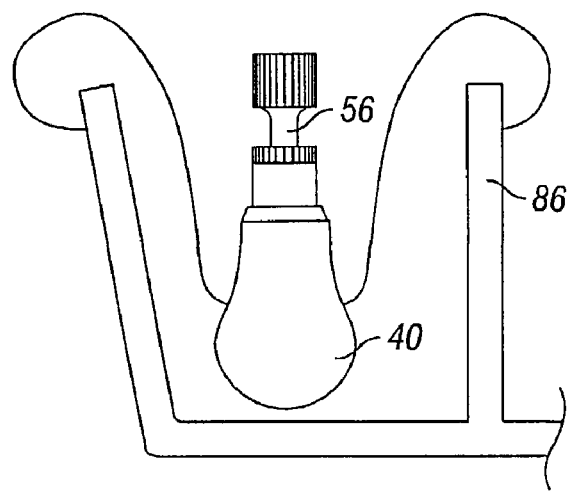
FIG. 17 is a schematic illustration of an analog-abutment inserted within the impression of FIG. 16.
Figure 18:
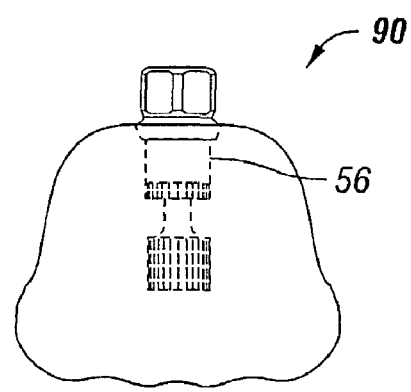
FIG. 18 is a schematic illustration of a model formed as part of the process of attachment of the dental implant system.

Referring to FIG. 17, and in the process depicted therein, an analog-abutment 56 is inserted into the matching cavity of the healing ball 40 contained within the impression material. As previously described, the analog-abutment 56 replicates the configuration of the implant abutment device 10 of the present invention. With the analog-abutment 56 seated in the healing ball 40, an impression is then poured in a rigid stone or plaster material to form the final model 90. In general, the entire analog-abutment 56, excluding its head 58 or head 58 and neck 60, may be buried in the final working model 90. As such, the remaining exposed portion of the analog-abutment 56, together with the impression material, forms an accurate and visible replica of the edentulous space within the patient's mouth prior to restoration, as shown in FIG. 18.

Figure 19:
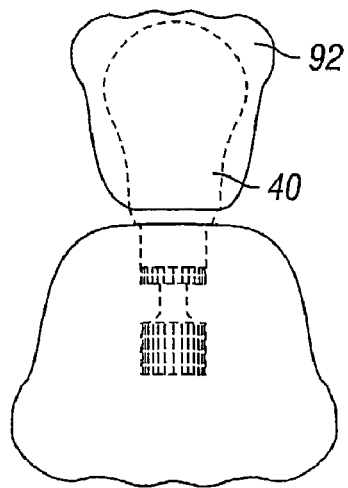
FIG. 19 is a schematic illustration of one embodiment of a prosthesis formed as part of the process of attachment of the dental implant system.

Referring to FIG. 19, a healing ball 40, coping (such as a preformed coping in the shape of a healing ball 40, tooth or other shapes) or metal framework may be used as part of the final prosthesis 92. Some of the materials used to form the final prosthesis include, but are not limited to, metal, metal alloys, ceramics, composites, aluminum oxide, fiber core, zirconium and other materials. The final prosthesis 92 may be formed using a lost wax technique, laser scan generated images, optical impression, CAD/CAM manufacturing, reverse engineering, rapid prototyping and other conventional techniques or methods. Once complete, the final prosthesis 92 is then installed within the patient's mouth using cement, retaining screws, or other attachment means known to those skilled in the art.

In an alternate embodiment (not shown), two or more implant-abutment devices 10 may be used for a single tooth (e.g., molar) restoration. The use of multiple implant-abutment devices 10 for a single tooth restoration provides greater support and stability for the final prosthesis. In addition, this configuration provides improved osseointegration and greater device surface area, which also improves the retentive strength of the prosthesis.

A multiple tooth or full-mouth reconstruction method of the present invention is similar to the single tooth reconstruction method. However, as previously described, multiple tooth or full-mouth reconstruction procedures are more involved, requiring common paths of insertion, sufficient friction to ensure a firm fit and no undue soft tissue tension.

Figure 20:
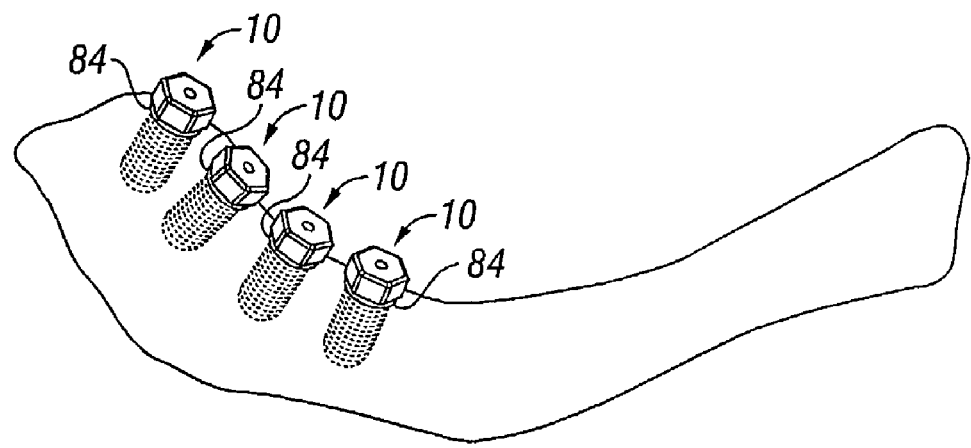
FIG. 20 is a schematic illustration of multiple implant-abutment devices inserted within the jawbone of a patient.

In one embodiment, the incision 80, hole 84 and implant-abutment device 10 insertion are made in a manner similar to that previously described for the single tooth reconstruction method. However, the approach is modified to accommodate multiple restorations. For example, the incision 80 may be larger, multiple holes 84 are generally created within the jawbone of the patient, and, likewise, multiple implant abutment devices 10 are inserted within the holes 84, as generally shown in FIG. 20. The four-teeth reconstruction shown in FIG. 20 is for illustration purposes and not meant to limit the scope of the claimed invention.

After adequate soft tissue healing has occurred and a stable recess for the prosthesis has been formed using healing balls 40 as previously described, the temporary prosthesis or original healing balls 40 are removed from each device 10.

In one embodiment, a pattern resin or similar material may be used to lute or connect all the healing balls 40 together as one unit, forming a coping framework. This process may be used for both the original healing balls 40 and the new healing balls 40.

Next, an impression is taken using an appropriately sized impression tray 86.

Figure 21:
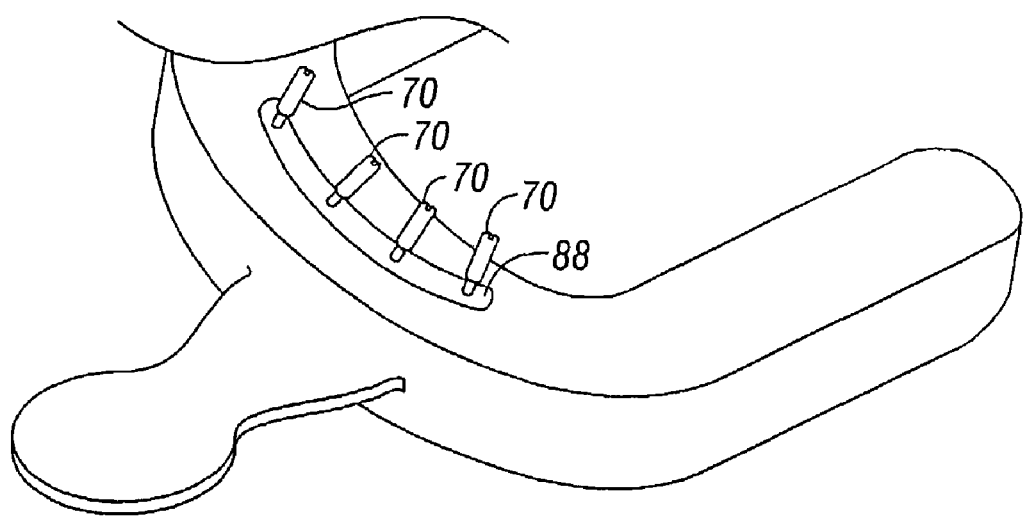
FIG. 21 is a schematic illustration of another embodiment of an impression tray.
Figure 22:
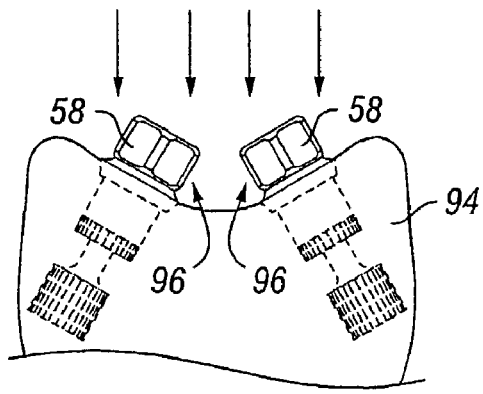
FIG. 22 is a schematic illustration of one embodiment of an alignment of multiple implant abutment devices of a dental implant system.
Figure 23:
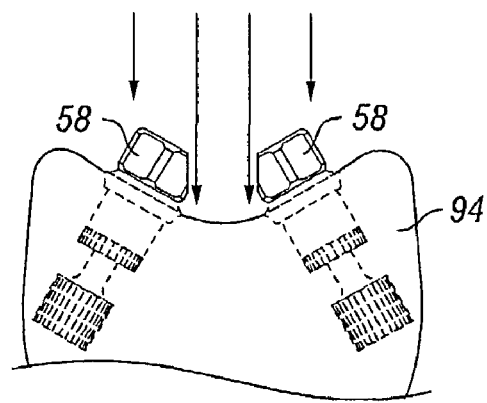
FIG. 23 is a schematic illustration of another embodiment of multiple implant-abutment devices modified as part of the methods of attachment of the dental implant system.

The protruding portions of the guide pins 70 extend through the opening(s) 88 in the impression framework, as shown in FIG. 21. Alternatively, a traditional disposable stock tray (not shown) may be used. As such, after all the healing balls 40 are luted or splinted together thereby forming a "picket-fence" type effect, the guide pins 70 can be removed from the healing balls 40. The healing balls 40 will remain in position and form a stable framework due to the "picket-fence" effect and remain in proper alignment with each other. Impression material can then be injected under and around the healing balls 40.

Figure 24:
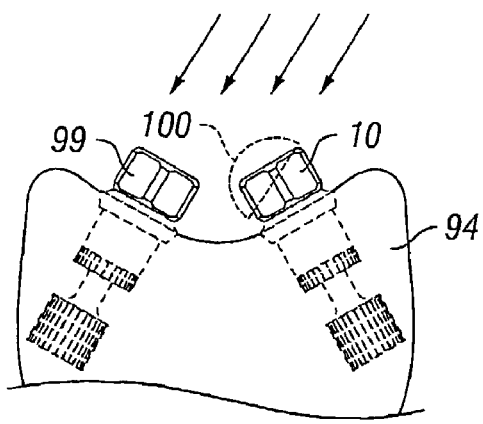
FIG. 24 is a schematic illustration of yet another embodiment of multiple implant-abutment devices modified as part of the methods of attachment of the dental implant system.

After the impression material has set, the guide pins 70, tray 86 and impression material are removed from the patient's mouth. The resulting impression includes the healing balls 40 incorporated in the impression material. The low height or minimal profile of the head 12 of each device 10 and flexibility of the impression media allow an accurate impression to be made, without permanent distortion or damage. In particular, the healing balls 40, as integral parts of the impression, may be cleanly withdrawn from the devices 10 without disturbing the precise relationship of each 20 device 98. The other devices 10 are then modified (e.g.. portion 100, shown in the FIG. 24 as encircled by a dashed line, is removed) according to the inclination/alignment of these devices 10 in relationship to the reference device 98 to ensure a secure and accurate fit for the final prosthesis.

Healing balls 40, copings or metal frameworks are then installed on the modified heads 58 of the stone model 94 and may be used as part of the final prosthesis. As previously described, the final prosthesis may be formed using a lost wax technique, laser scan generated images, optical impression, CAD/CAM manufacturing, reverse engineering, rapid prototyping and other conventional techniques or methods.

With the final stone model 94 as a guide, the corresponding surfaces of the device heads 12 in the patient's mouth are removed. After a passive placement is achieved, the final prosthesis is then installed using cement, retaining screws or other attachment means to stabilize and secure the prosthesis within the patient's mouth.

In an alternate embodiment of the invention, a template (not shown) together with the final stone model 94 is used as a guide for removing the necessary portions/surfaces of the device heads 12 in the patient's mouth. The template may be one or more copings, caps, framework or other types of coverings linked or connected together to maintain alignment of the caps to each other and to their counter-part analog-abutments 56 in the final stone model 94. The template may be made of a variety of materials including, but not limited to, metals, metal alloys, plastics, ceramics, composites and other materials, including combinations of materials.

Further, each cap may be a variety of configurations (such as, for example, cylindrical, spherical, hexagonal, polygonal and other configurations), provided the cap configuration matches to securely engage its corresponding analog-abutment configuration.

The following example and associated figures will reference only a single cap in a template and a single analog-abutment 56 in a final model 94, however it is understood that the template and final model 94 include one or more caps and analog abutments 56, respectively.

Figure 25:
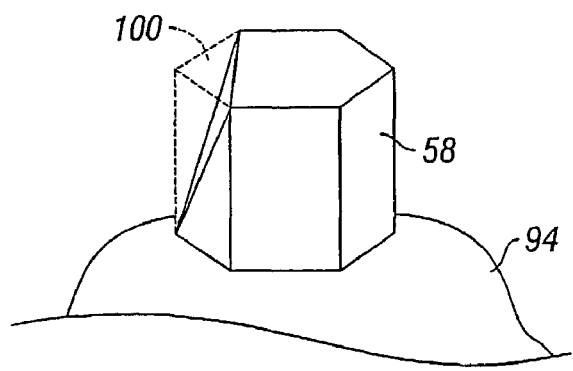
FIG. 25 is a schematic illustration of another embodiment of a modified implant-abutment device.
Figure 26:
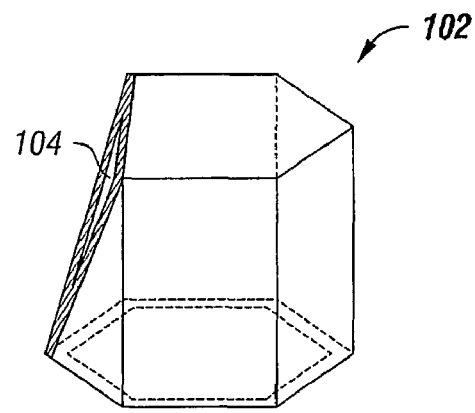
FIG. 26 is a schematic illustration of a section of a template of the dental implant system.

As previously disclosed, the cap of the template replicates its counterpart head 58 of the analog-abutment 56 in the final model 94. Referring to FIG. 25, a portion 100 (shown in phantom on FIG. 25) of the analog-abutment head 58 in the final model 94 is removed or modified as previously described. The corresponding portions 22 of its matching cap 104 are then also removed, forming a window or some other type of opening 104 in the cap 102 that corresponds to the modified area of the head 58, shown in FIG. 26.

Figure 27:
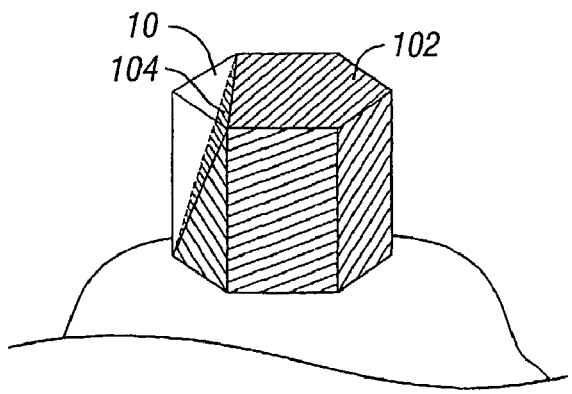
FIG. 27 is a schematic illustration of one embodiment of a section of a template positioned on an implant-abutment device.

As shown in FIG. 27, when the cap 102 is properly positioned or placed over the patient's corresponding implant-abutment device 10, portions of the device 10 protruding through the opening 104 correspond to the removed portions of the analog abutment 100. At this point, the user may use an appropriate tool to remove the protruding portions of the device 10. Alternatively, the user may simply mark the portions of the device 10 that need to be modified, remove the cap and then remove/modify the marked portions of the device 10. Other methods of modifying the device 10, including the cap 102, not specifically disclosed but known in the art may also be used.

The quantity of components and associated reconstruction methods of the dental implant system of the present invention are greatly reduced and simplified compared to conventional implant systems and methods of use. Especially in multiple implant situations, the dental implant system of the present invention greatly reduces the number of clinical procedures and total treatment time. In particular, the amount of time between the initial surgery to the tooth/prosthesis mounting is greatly reduced.

Further, the procedures or methods of the present invention are also more predictable with respect to cosmetic and functional effects of the final prosthesis when compared to traditional approaches. As such, the dental implant system of the present invention may reduce post-operative infection, improve device/prosthesis strength and prolong its stability and reduce the overall time for a reconstruction procedure by approximately three months or more. In addition, the dental implant system and associated methods of the present invention enable a practitioner to form a final prosthesis, including an infinite number of facsimiles of said final prosthesis (for example, as spares or replacements if the original prosthesis should become damaged or lost), based on a single impression. In general, the overall procedure using the dental implant system of the present invention is fast, simple and effective.

Figure 28:
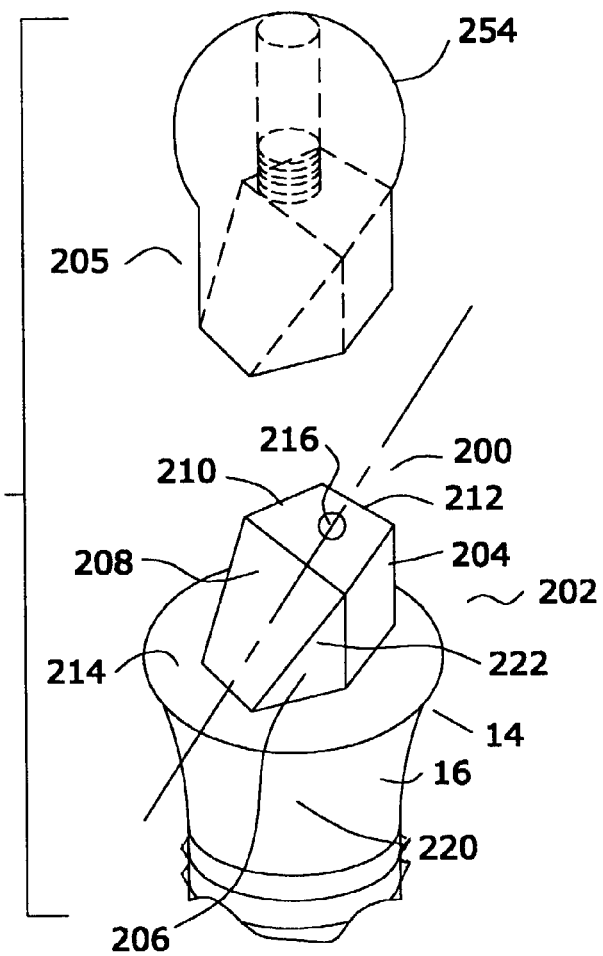
FIG. 28 is an exploded view of an embodiment of an abutment used in the device of this invention.
Figure 29:
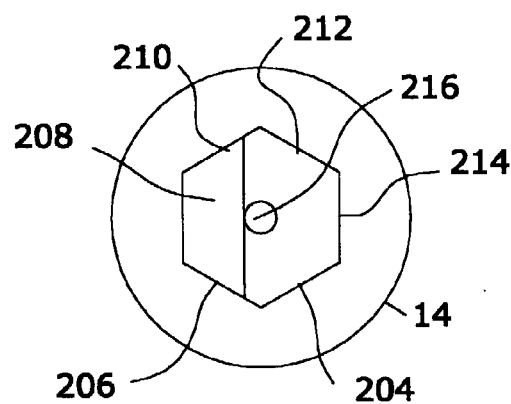
FIG. 29 is top view of the abutment of FIG. 28.

FIG. 28 is a partial exploded view of an dental implant assembly 200 comprised of a head 202 which facilitates the use of assembly 200 in multiple implant restorations.

Referring to FIG. 28, and in the preferred embodiment depicted therein, it will be seen that head 202 is comprised of sides 204, 206, 208, 210, and 212. Each of these sides intersects with surface 214 of neck 14.

Figure 34A:
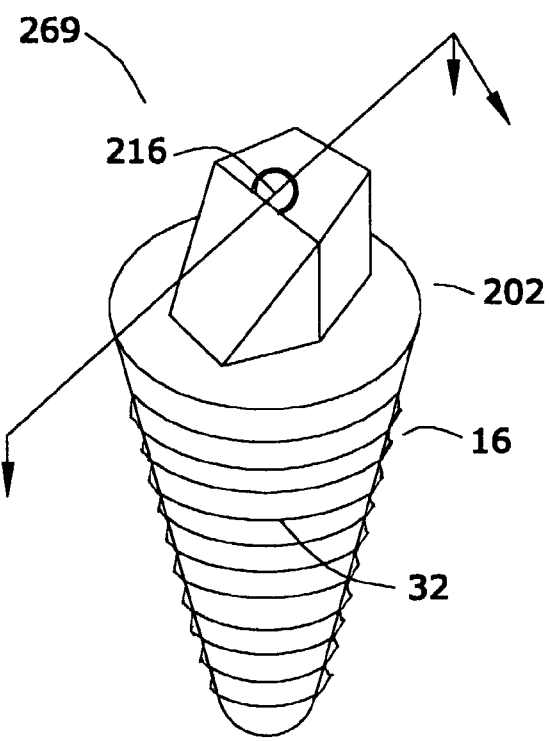
FIG. 34A is a perspective view of another implant assembly of the invention.
Figure 34B:
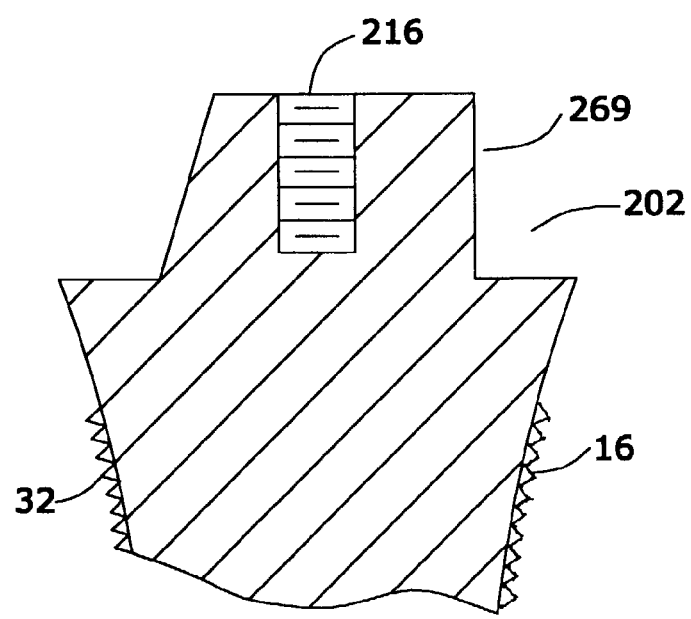
FIG. 34B is a sectional view of another implant assembly of the invention.

In one embodiment, illustrated in FIGS. 34A and 34B, the neck 14 is omitted and the head 202 is directly contiguous with base 16.

Referring again to FIG. 28, and in the preferred embodiment depicted therein, with the exception of side 208, each of the other sides forms an angle vis-à-vis surface 214 that is substantially perpendicular, ranging from about 80 to about 100 degrees and, more preferably, from about 75 to about 95 degrees. However, the side 208 forms an angle with surface 214 of less than about 75 degrees.

In the embodiment depicted in FIG. 28, there are at least five sides that intersect surface 214 at a substantially perpendicular angle. Devices with more of such sides may be used, provided that at least two sides of the head 202 are substantially perpendicular to the surface 214 and at least one side forms an angle with such surface of less than about 75 degrees. In one embodiment, at least three such sides of the head 202 are substantially perpendicular to the surface 214. In another embodiment, at least four such sides of the head 202 are substantially perpendicular to the surface 214. In yet another embodiment, at least five such sides of the head 202 are substantially perpendicular to the surface 214.

In another embodiment, not shown, at least two of sides of the head 202 form an angle of from about 60 to about 100 degrees with the surface 214.

Referring again to FIG. 28, a bore 216 extends from the top surface of the head 202 to a distance of from about 2 to about 5 millimeters. In one embodiment, the bore 216 is threaded.

In another embodiment, not shown, the bore 216 is omitted from the head 202. In another embodiment, not shown, the bore 216 is replaced by an annular groove disposed beneath substantially polygonal portion of head 202 and surface 214. In one embodiment, the bore 216 is substantially coaxial with the axis 220 of base 16. In another embodiment, illustrated in FIG. 28, the bore 216 is not coaxial with the axis 220 but, instead, forms an angle that is less than 45 degrees and, in one embodiment, is substantially identical to the angle formed by side 208 with surface 214.

Figure 28A:
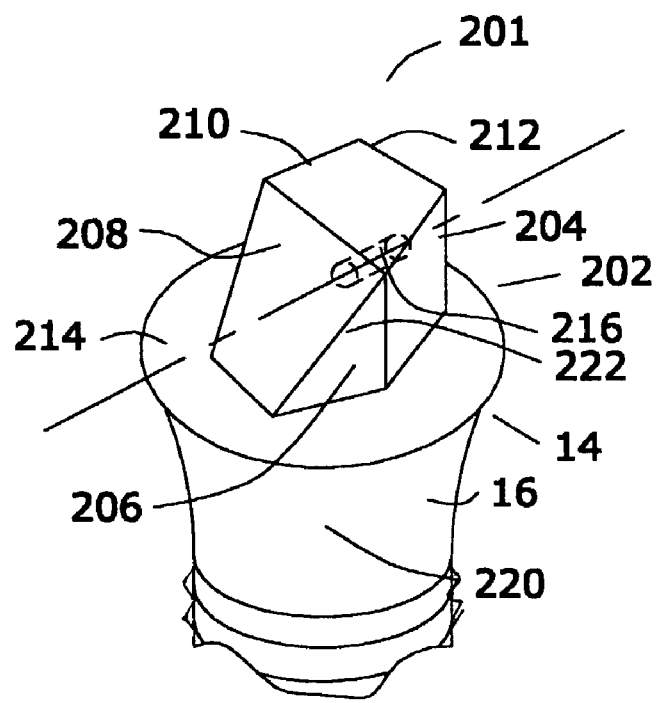
FIGS. 28A and 28B are perspective views of other abutment assemblies.
Figure 29A:
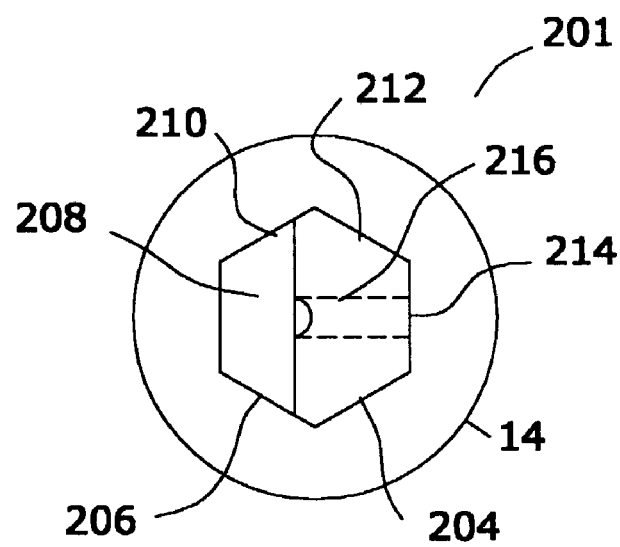
FIGS. 29A and 29B are top views of other abutment assemblies.

FIGS. 28A and 29A disclose a dental implant assembly 201 which is similar to the assembly 200 but differs therefrom in that the bore 216 is substantially perpendicular to the axis 220.

Figure 28B:
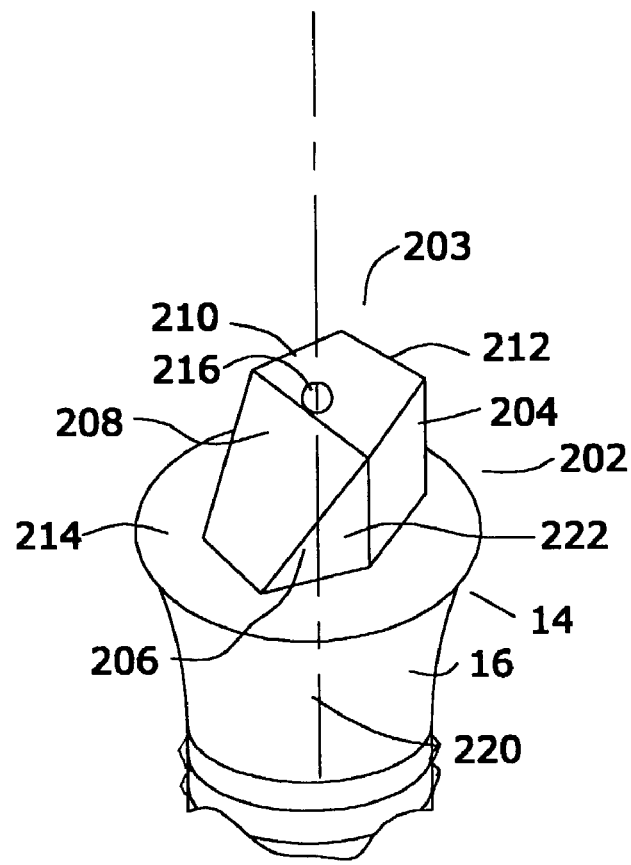
Figure 29B:
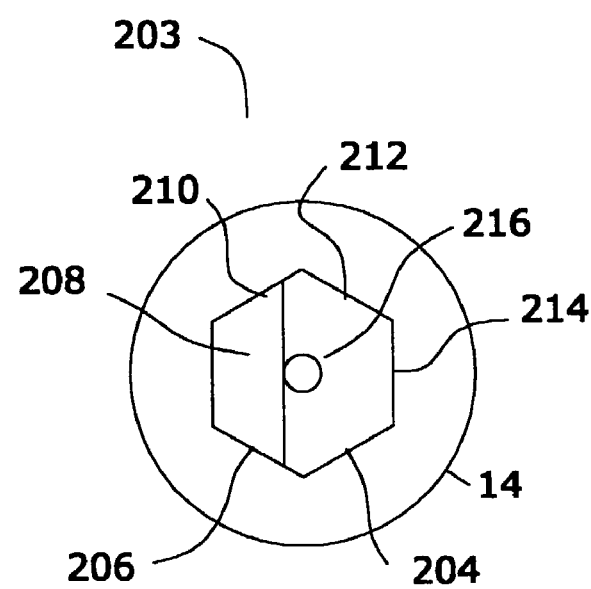

FIGS. 28B and 29B disclose a dental implant assembly 203 which is similar to the assembly 200 but differs therefrom in that the bore 216 is substantially parallel to the axis 220. In the embodiment depicted, bore 216 is also substantially coincident with the axis 220.

Referring again to FIG. 28, it will be seen that a healing ball 205 is adapted to fit over the head 202. A similar healing ball 205 may be used in the embodiments depicted in FIGS. 28A and 28B but has been omitted therefrom for the sake of simplicity of representation.

The shape of the head depicted in FIGS. 29A and 29B may be varied. Some other suitable shapes are depicted in FIGS. 30A through 30H.

FIGS. 30A through 30H present a multiplicity of sectional views showing the shapes in which the head 202 may be. In the embodiments depicted, the shapes are either comprised of straight walls 230 and/or arcuate sections 232.

Figure 31A:
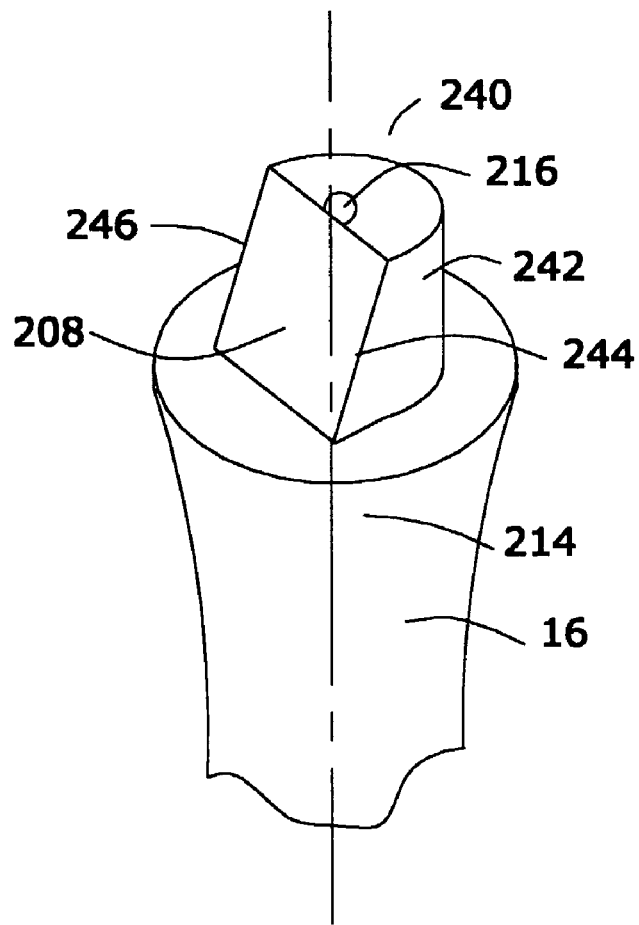
FIGS. 31A and 31B are perspective and top views, respectively, of another implant assembly of the invention.
Figure 31B:
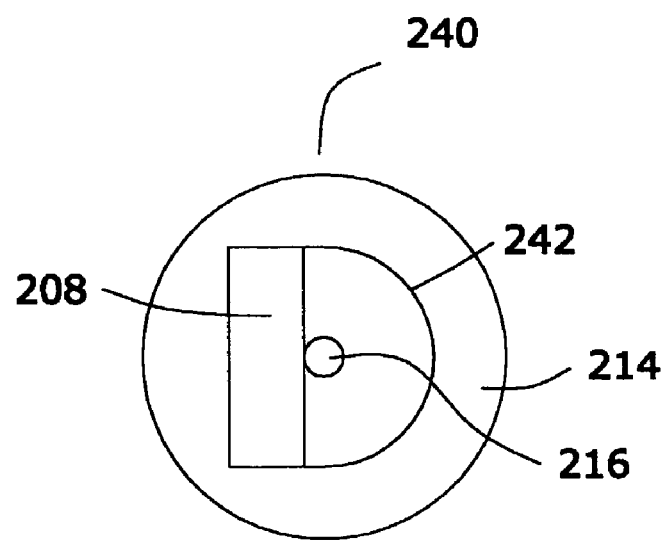

FIGS. 31A and 3B are perspective and top views, respectively, of an assembly 240 in which arcuate section 242 joins walls 244 and 246 of inclined section 208. As will be apparent, because arcuate section 242 theoretically contains an infinite number of walls, the structure 240 meets the requirement that at least two such walls are substantially perpendicular to the surface 214 of base 16.

Figure 32:
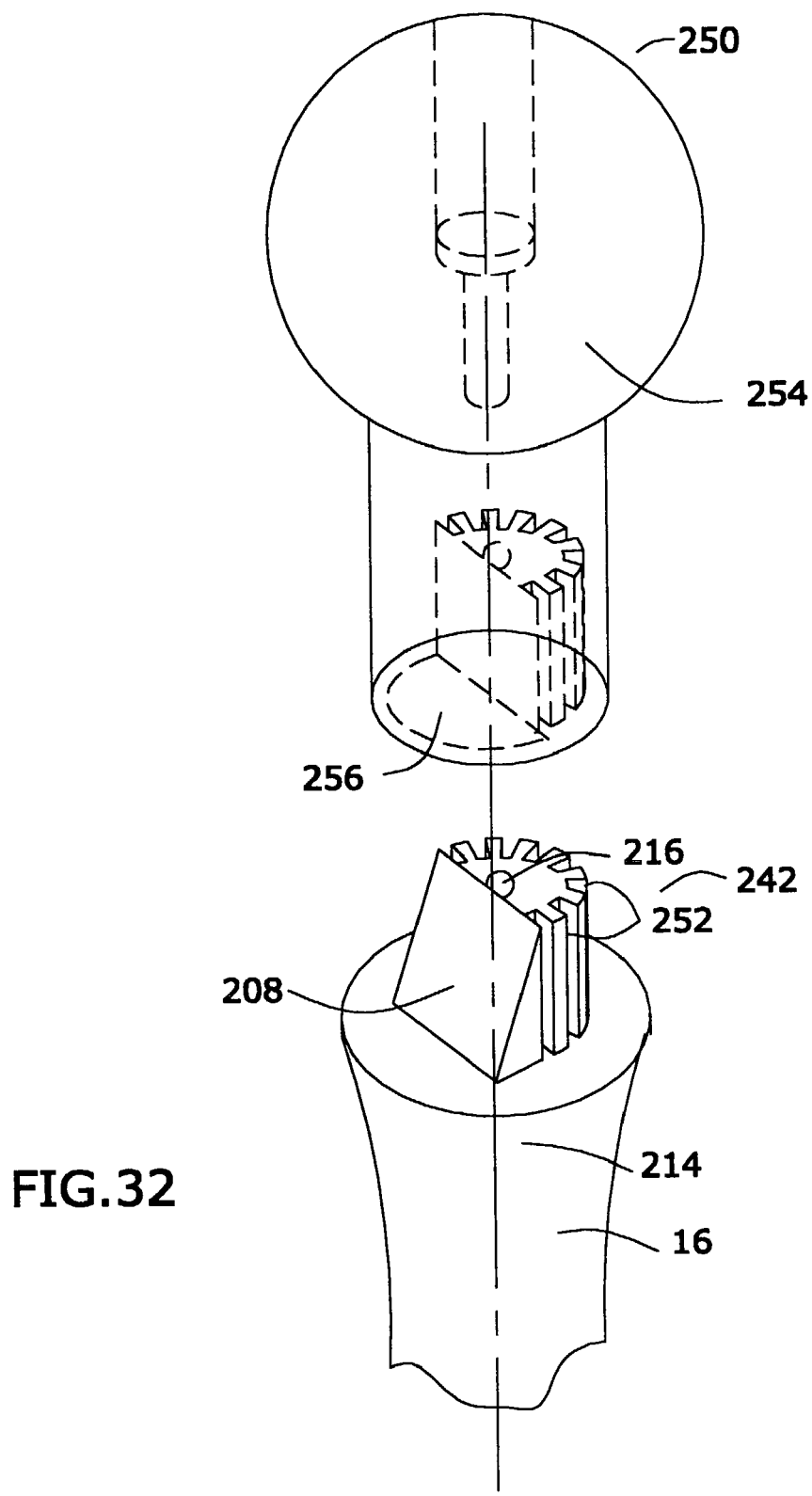
FIG. 32 is an exploded schematic view of a preferred implant assembly of the invention.

FIGS. 32 disclose an exploded view of an assembly 250 that is similar in configuration to the assembly 240 but differs therefrom in that arcuate section 242 is comprised of a multiplicity of splines 252. In the configuration depicted in FIG. 32, such splines 252 have a substantially rectangular cross-sectional shape.

Referring again to FIG. 32, and in the preferred embodiment depicted therein, it will be seen that healing ball 254 preferably is comprised of an orifice 256 that is adapted to receive the section 208 and the splines 252.

Figure 32A:
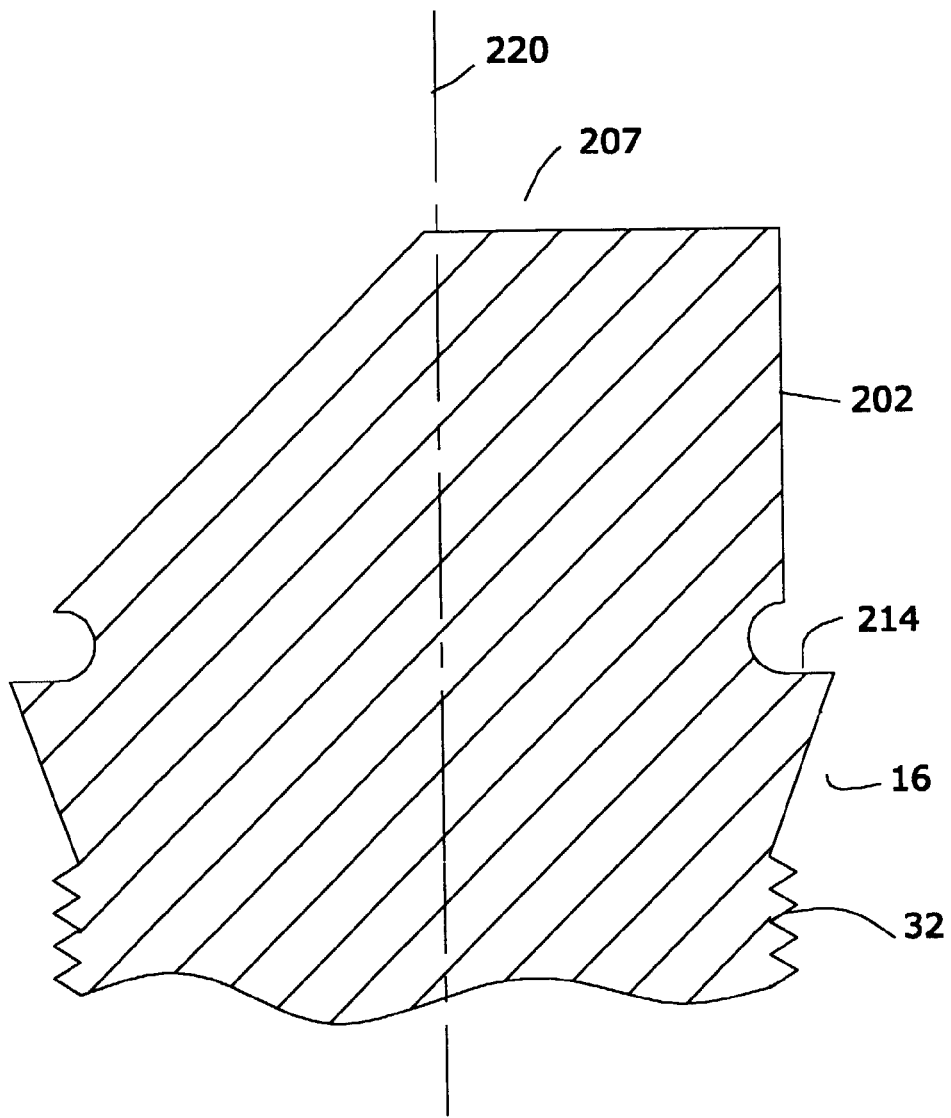
FIGS. 32A and 32B, are sectional views of preferred abutment assemblies of the invention.

FIG. 32A is a partial sectional view of a implant assembly 207 that is similar to the implant assembly 201 (see FIG. 28A) but omits that omits the orifice 216.

Figure 32B:
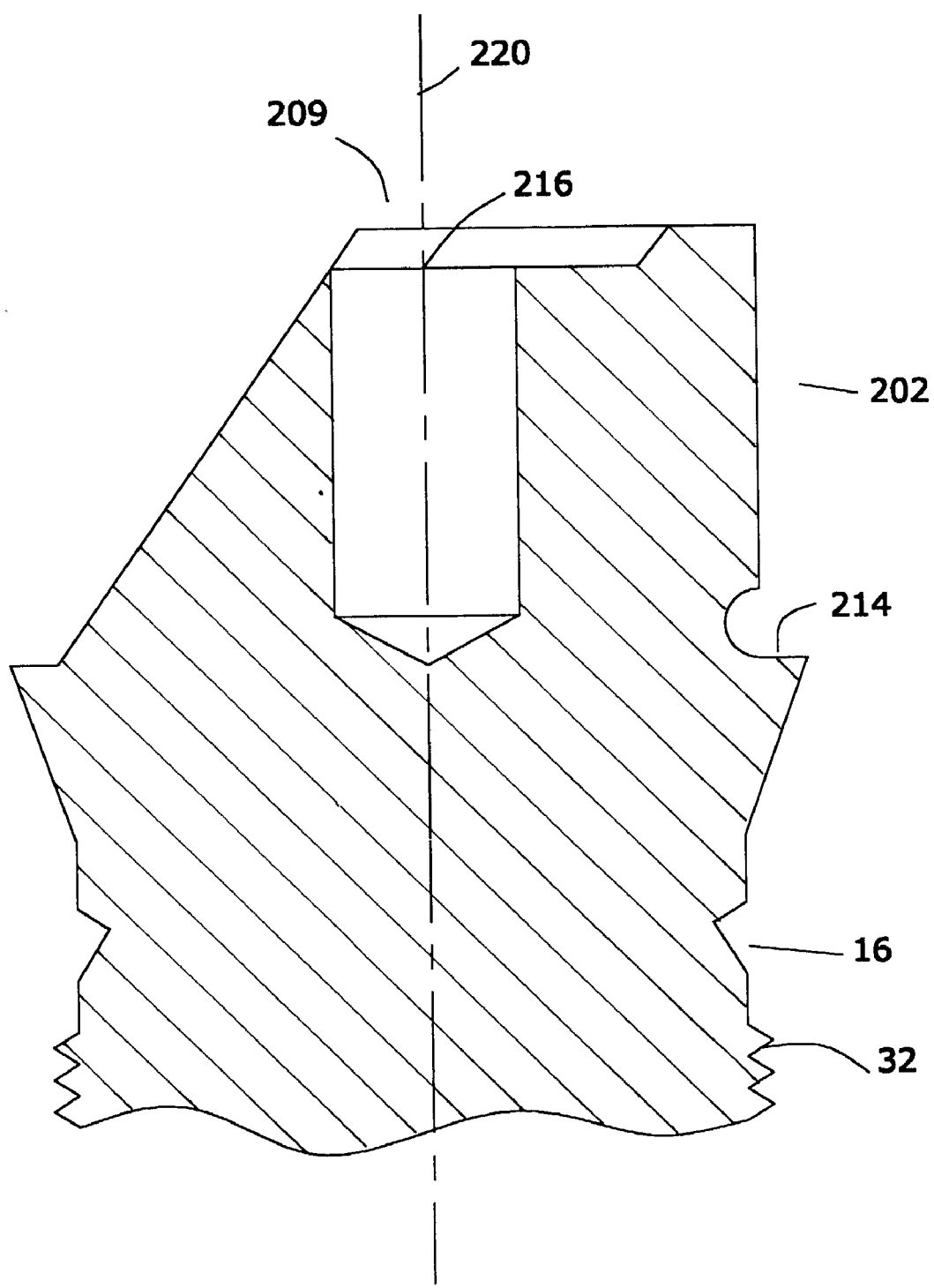

FIG. 32B is a partial sectional view of an implant assembly 209 that is similar to the implant assembly 201 (see FIG. 28A) but differs therefrom in that it does contain an orifice 216 that is substantially aligned with the axis of the device 209.

As will be apparent from FIGS. 33A through 33H, different splined arrangements may be used with the device 250.

Figure 33A:
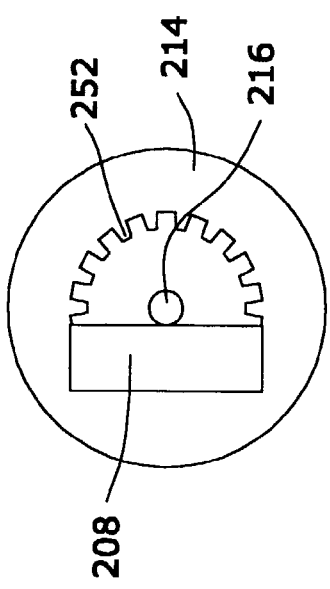
FIGS. 33A, 33B, 33C, 33D, 33E, 33F, 33G, and 33H are top views of other preferred abutment assemblies of the invention.
Figure 33B:
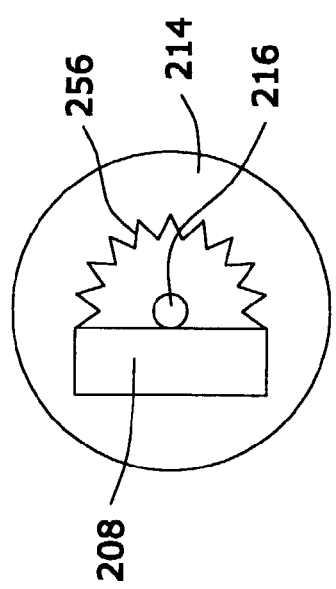
Figure 33C:
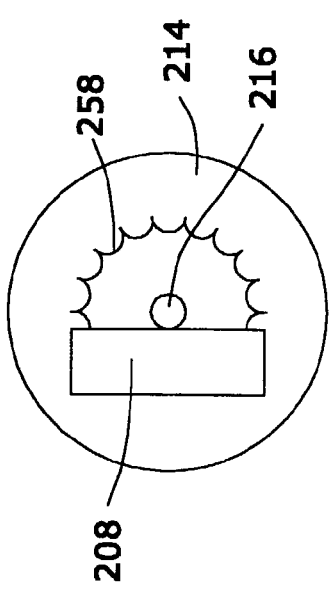
Figure 33D:
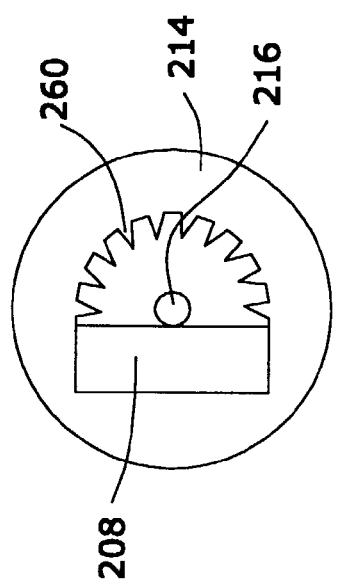
Figure 33E:
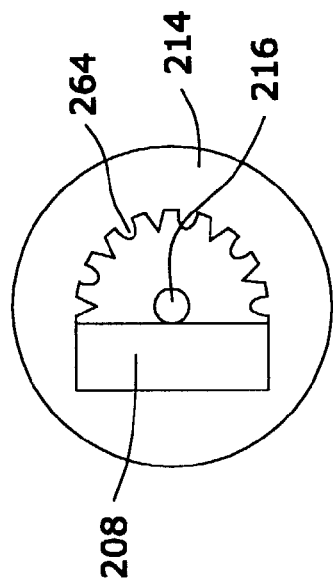
Figure 33F:
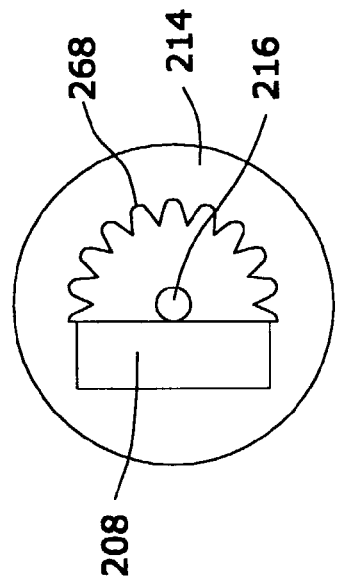
Figure 33G:
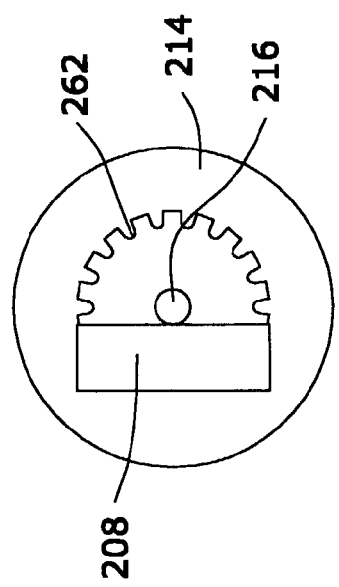
Figure 33H:
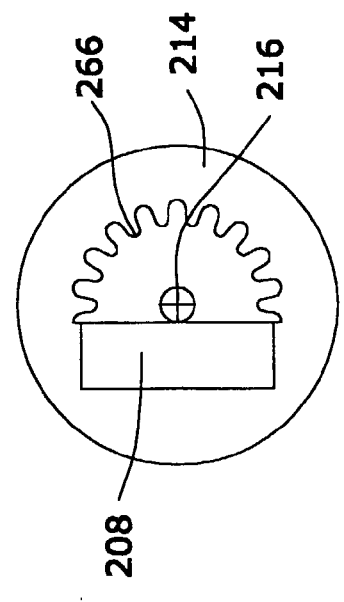

Thus, as depicted in FIG. 33A, the splines 252 may have a substantially rectilinear cross-sectional shape. As depicted in FIG. 33B, the splines 256 may have a substantially triangular cross-sectional shape. As depicted in FIG. 33C, the splines 258 may have a substantially circular cross-sectional shape. As depicted in FIG. 33D, the splines 260 may have a substantially polygonal cross-sectional; in the embodiment, depicted, this shape is formed by alternating rectangles and triangles. As depicted in FIG. 33E, the splines 262 may have a shape defined by a linear section and an arcuate section; in the embodiment depicted, the splines 262 are formed by alternating semicircles and flat surfaces. As depicted in FIG. 33F, the splines 264 may have different shapes which may alternate on the splined surface; thus, e.g., they may contain both triangular, circular, and composite shapes in which flat top intersects two adjacent splines. The splines 266 depicted in FIG. 33G are defined by half-circles joined by arcuate tops. By comparison, the splines 268 depicted in FIG. 33H are defined by triangular sections joined by arcuate tops. Many other splined shapes, not shown, also may be used.

Figure 35:
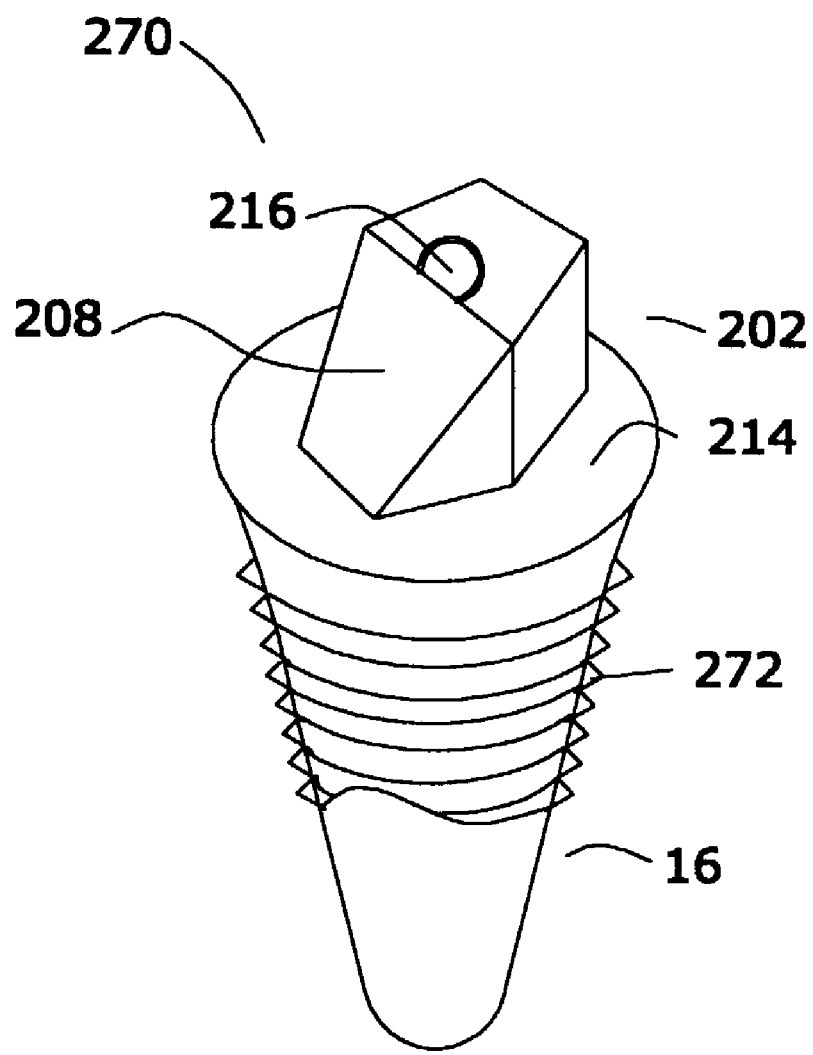
FIGS. 35, 36, 37A and 37B are perspective views of other implant assemblies of the invention.

FIG. 35 is a perspective view of an implant assembly 270 that similar to the implant assembly 269 of FIGS. 34A and 34B but differs therefrom in that the surface 272 of base 16 is roughened.

In one embodiment, the surface 272 is roughened in accordance with the acid-etching procedure disclosed in International patent publication WO 96/16611. In the process described in this patent publication, the surfaces of the implant body are exposed to an acidic etching process after the natural titanium oxide layer is removed to attain an essentially uniform roughness over the entire surface (WO 96/16611). applicant's U.S. Pat. No. 5,733,124, the entire disclosure of which is hereby incorporated by reference into this specification.

In another embodiment, the surface 272 is roughened in accordance with the procedure disclosed in an article by Cochran et al., "Bone response to unloaded and loaded titanium implants with a sand-blasted and acid-etched surface", Journal of Biomedical Materials Research, Vol. 40, 1998, p.1. In this process, the surface 272 is subjected to coarse sand blasting to create macroroughness in the titanium. This process is followed by acid etching that generates evenly-distributed micropits in the sand-blasted surface.

One may roughen such surface 272, or other surfaces, by conventional means known to those skilled in the art. Thus, e.g., one may use the roughening processes disclosed in U.S. Pat. Nos. 5,588,838 of Hannson (microroughness having a height between 0.02 to about 0.2 millimeters), 5,607,480 of Beaty (individual depressions and dents with transverse dimensions about half of the size of impacting grit particles, on the order of 5–10 microns), 5,947,735 (additive and subtractive roughening), 5,897,027 of Wagner et al. (surface roughness of from about 7 t to about 300 microinches), 6,344,061 of Leitao et al. (surface roughness with an average peak distance between 10 and 1,000 nanometers), 6,095,817 of Wagner et al., and the like. The entire disclosure of each of these United States patents is hereby incorporated by reference into this specification.

One preferred means for providing the desired degree(s) of roughness to the implant assembly of this invention is described below. The process described below is especially advantageous for use with one-piece implant assemblies.

In this process, all abutment areas are preferably completely covered by soft wax to get a demarcation and to protect the abutment portion of the one piece implant from sandblasting and etching.

Figure 36:
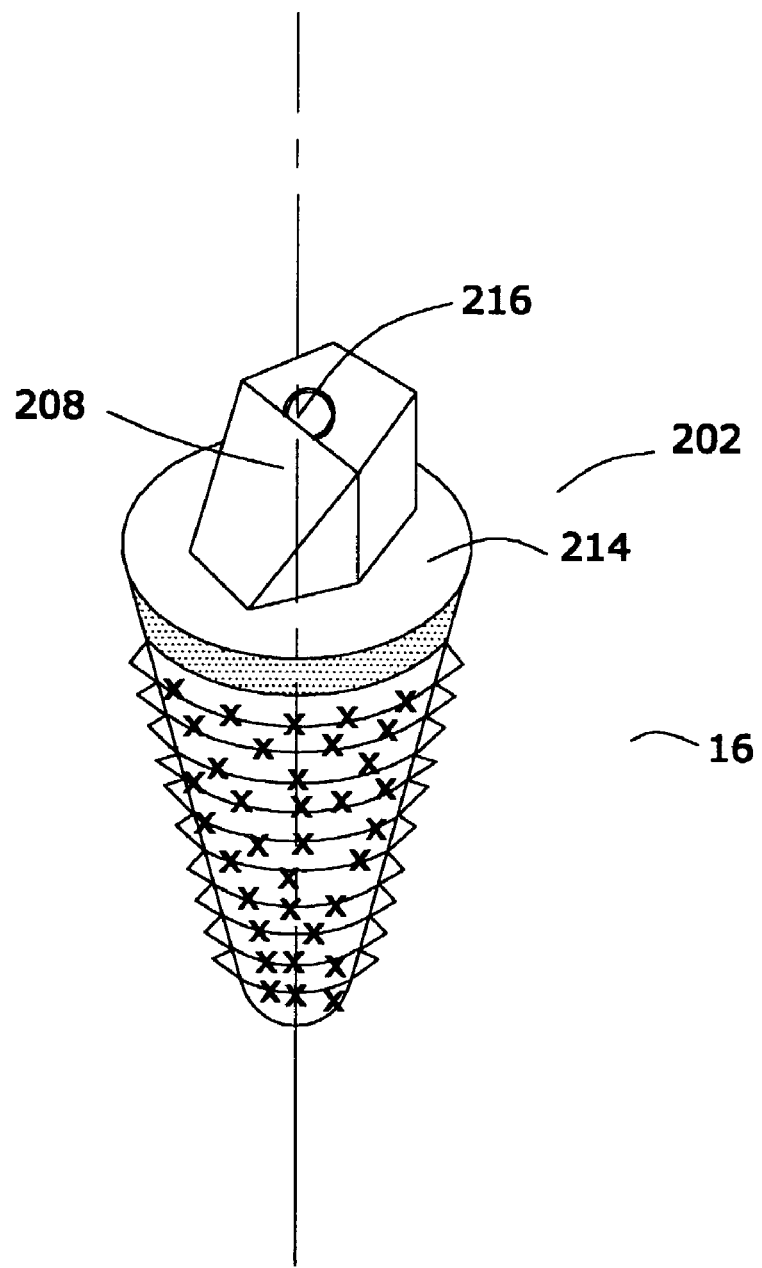

Waxing of the implant abutment assembly involves insertion of a guide pin into orifice 216 (see FIG. 36). The implant assembly is then placed into a pre-drilled Pro-form laminate plate Wax is then heated on a hot plate to a temperature sufficient to melt the wax and liquefy it.

A masking device, such as a plate, is used to separate and isolate the top part of the implant assembly from its bottom part. The plate is preheated to a temperature of about 70 degrees Centigrade for about 10 minutes. Thereafter, wax is poured over the masked implant assembly and allowed to cool for from about 30 to about 45 minutes.

Thereafter, the assembly is cooled in a refrigerator for from about 10 to about 15 minutes. The partially masked implant assembly that is partially embedded in wax is then subjected to sandblasting.

Thereafter the exposed portion(s) of the one-piece implant assembly is grit blasted using a Renfert sandblaster with non-recycled aluminum oxide (50 micron size) to remove burrs and metallic contaminants. The sand-blasted assembly is then subjected to acid etching.

In one embodiment, acid etching is accomplished with the use of an acid solution composed of a 10–30 volume percent (150–450 g/l) of 70% nitric acid and 1:3 volume percent (12 to 36 g/l) of 48% hydrofluoric acid (maintaining a ratio of 10 parts nitric acid to 1 part hydrofluoric Acid). The surface of the implant assembly to be acid etched is contacted with the acid mixture while being subjected to ultrasonic energy for 3 minutes.

Figure 37B:
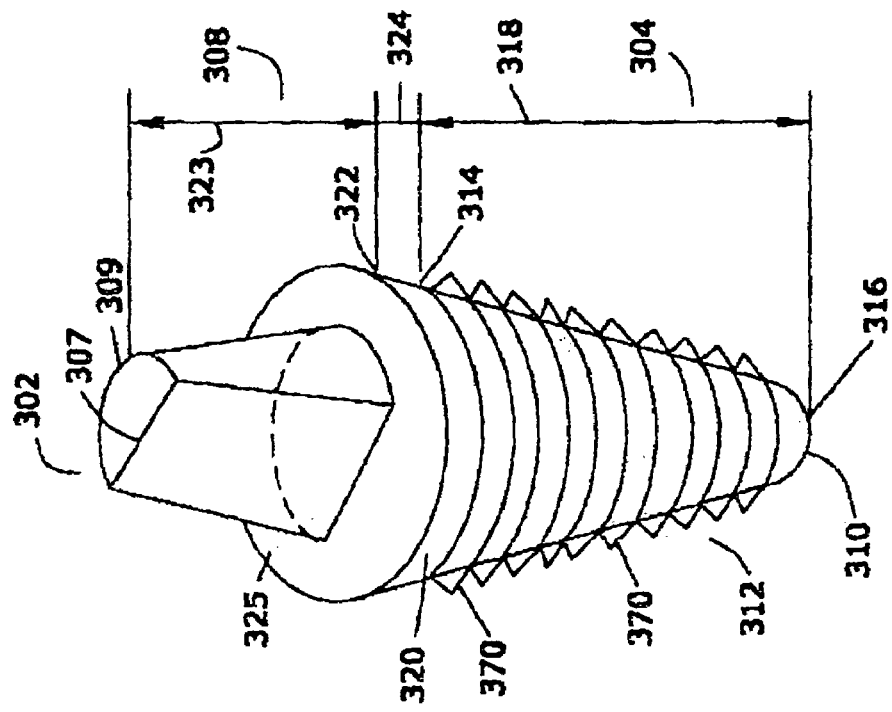
Figure 37A:
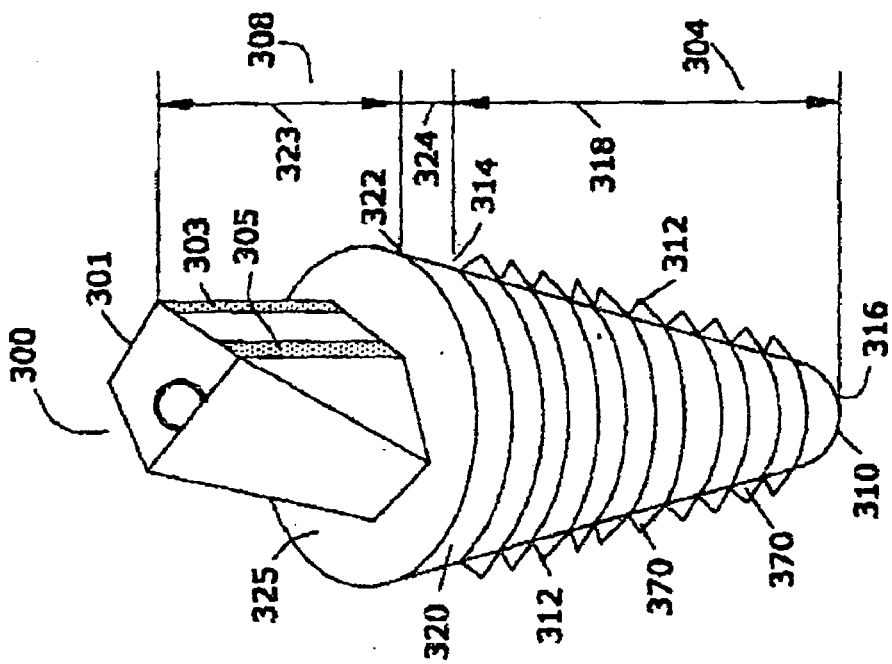

FIGS. 37A and 37B illustrate two preferred devices which may be made by the process of this invention. Referring to these Figures, it will be seen that each of implant assemblies 300 and 302 is comprised of base section 304, and ledge section 320, and head section 308.

In each of implant assemblies 300 and 302, the base section 304, the ledge section 320, and the head section 308 are integrally joined to each other.

In each of implant assemblies 300 and 302, the head section 308 has a cross-sectional shape formed by alternating arcuate and linear walls; similar devices are disclosed in U.S. Pat. No. 5,733,124, the entire disclosure of which is hereby incorporated by reference into this specification.

Referring to implant assembly 300, one of the linear walls is wall 301, and the arcuate walls are walls 303 and 305.

Referring to implant assembly 302, the linear wall is wall 307, and the arcuate wall is wall 309.

Each of implant assembles 300 and 302 is comprised of a base 304 that extends upwardly and outwardly from its bottom 310 to its top 312.

In the preferred embodiments depicted in FIGS. 37A and 37B, the base 304 is preferably comprised of two distinct sections. The first such section 312, extending from point 314 to point 316, has a length 318 of from about 3 to about 50 millimeters and, preferably, from about 7 to about 17 millimeters. The second such section 320, extending from point 314 to point 322, has a width 324 of from about 0.0 to about 2 millimeters and, preferably, from about 0.3 to about 0.7 millimeters.

It is preferred that section 320 have a width 324 that is no greater than about 15 percent of the length 318 of section 312 and, more preferably, is less than about 10 percent of the length 318 of section 312.

In both of the embodiments depicted in FIGS. 37A and 37B, the section 312 has a substantially rougher surface than the section 320.

Figure 38:
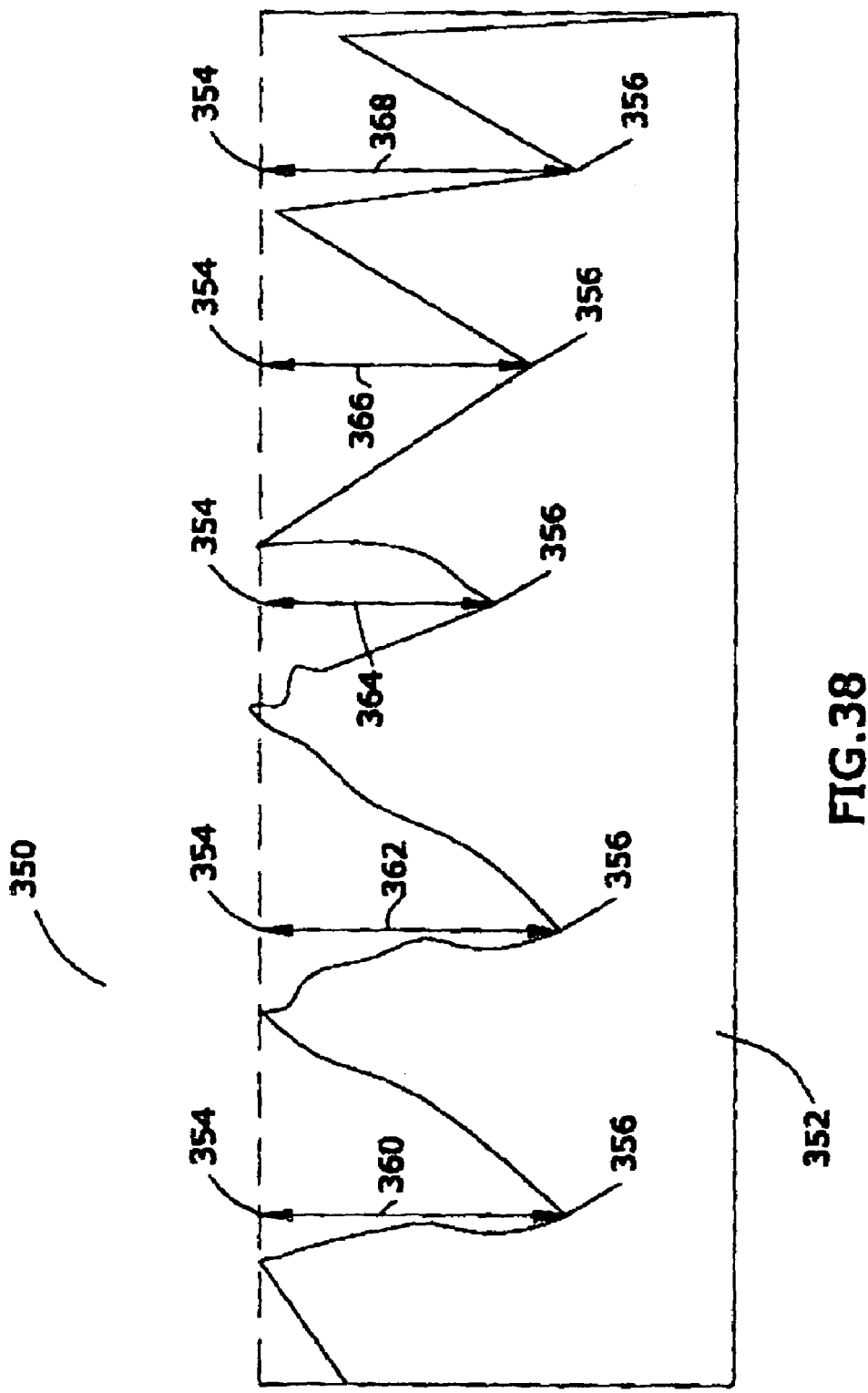
FIG. 38 is a sectional view of a roughened surface.

FIG. 38 is a sectional rough of a roughened surface 350 formed in a substrate 352. As will be seen, this roughened surface 350 is comprised of a multiplicity of peaks 354 and valleys 356. The distances 360, 362, 364, 366, 368 between the peaks 354 and the valleys 356 indicate the roughness of surface 350. For the purposes of this specification, the roughness of any such surface is the average peak-to-valley distance of the surface. As is known to those skilled in the art, this may be measured by conventional techniques, such as, e.g., scanning electron micrography.

Referring again to FIGS. 37A and 37B, and in the preferred embodiment depicted therein, the section 312 will preferably have an average roughness (i.e., an average peak to valley distance of its indentations) of from about 10 to about 1,000 microns and, preferably, from about 20 to about 200 microns.

In this embodiment, the section 320 will preferably have an average roughness (i.e, an average peak to valley distance of its indentations) of from about 0.1 to about 100 microns.

The section 312 will preferably have an average roughness that is at least about 10 times as great as the average roughness of the section 320. In one embodiment, the section 312 has an average roughness that is at least about 50 times as great as the average roughness of section 320. In another embodiment, the section 312 has an average roughness that is at least about 100 times as great as the average roughness of section 320.

One may obtain the differential roughness properties described hereinabove by subjecting the sections 312 and/or 320 to different treatments and/or different lengths of treatment, masking one (with wax, e.g.) while treating another. Thus, for example, the section 312 may be treated with both sandblasting and acid etching, whereas the section 320 may be subjected to micromachining or laser etching.

Thus, e.g., one may use microtexturing to create the roughness in section 320. Reference may be had, e.g., to U.S. Pat. Nos. 6,228,434, 5,964,804, 5,782,912, 5,349,503, 5,909,020, and the like. The entire disclosure of each of these United States patents is hereby incorporated by reference into this specification.

Thus, e.g., one may use laser etching to create the roughness in section 320. Reference may be had, e.g., to U.S. Pat. Nos. 5,164,324, 6,391,212, 6,277,312, 5,544,775, 5,018,164, and the like. The entire disclosure of each of these United States patents is hereby incorporated by reference into this specification.

In one embodiment, illustrated in FIGS. 37A and 37B, the roughened surface 312 is coated with a bioactive coating 370. The biological coating 370 is comprised of or consists essentially of a biological active material.

As is disclosed in U.S. Pat. No. 6,344,061, the substrate having the desired surface roughness can efficiently be coated in vitro with a layer of one or more biologically active agents; the entire disclosure of this United States patent is hereby incorporated by reference into this specification. . The composite coating can be relatively thin, in the order of from, e.g. 50 nanometers to 200 microns, especially from 1 to 50 microns. The biologically active agent in the coating includes, but is not limited to, single or combinations or proteins, lipids, (lipo)polysaccharides, growth-factors, cytostatic agents, hormones, and antibiotics. Examples of such agents are bone morphogenetic proteins (BMP's), basic fibroblast growth factor (bFGF), transforming growth factor (TGF-$\beta$), osteogenic growth peptide (OGP), et cetera. The molecular weight of said biologically active agents can vary from several tens of Daltons, to thousands of kilo-Daltons.

In one embodiment, at least a portion of the coated layer has a thickness greater than the average depth of the roughened surface. See, e.g., U.S. Pat. No. 6,344,061.

In another embodiment, the biologically active agent is selected from the group consisting of proteins, lipids, (lipo)polysaccharides, growth factors, cytostatic agents, hormones, antibiotics, and combinations thereof. See the aforementioned U.S. Pat. No. 6,344,061.

In yet another embodiment, the biologically active agent is selected from the group consisting of bone morphogenetic proteins, basic fibroblast growth factor, transforming growth factor, osteogenic growth peptide, and combinations thereof. See U.S. Pat. 6,344,061.

In one embodiment, the coating is comprised of one or more anions selected from the group consisting of hydroxide, chloride, sulphate, nitrate, and combinations thereof. In another embodiment, the coating further comprises one or more cations selected from the group consisting of hydrogen, sodium, potassium, magnesium, and combinations thereof. See, e.g., such U.S. Pat. No. 6,344,061.

In yet another embodiment, the sandblasting step is replaced by blasting with other abrasive material, such as alumina.

In yet another embodiment, the biologically active material is comprised of organic material comprising a multiplicity of amino acids and/or proteins.

In one embodiment, the organic material is an organic amine containing from about 1 to about 10 carbon atoms and from about 1 to about 4 amino groups. Some suitable materials in this embodiment include gamma-aminopropyletriethyoxysilane, allyl amine, carebodiimide, bone morphogenic protein, extracellular matrix proteins, and the like. Reference may be had, e.g., to articles by Wojcik et al. ("Biochemical surface modification . . . for the delivery of protein . . . , " Biomed Sc Instrum 1997;33: 166–171), by Puleo et al. ("A technique to immobile bioactive proteins . . . , " Biomaterials 2002 May; 23(9): 2079–2087), by An et al. ("Prevention of bacterial adherence to implant surfaces . . . , " J Orthop Res 1996 Sep; 14(5):846–849), by Bessho et al. ("BMP stimulation of bone response . . . ," Clin Oral Implants Res 1999 Jun; 10(3):212–8), by Deligianni et al. ("Effect of surface roughness of the titanium alloy . . . , " Biomaterials 2002 Jun; 22(11): 1241–1251), by Dean et al. ("Firbonectin and laminin enhance gingival cell attachment . . . , " Int J. Oral Maxillofac Implants 1995 Nov–Dec; 10(6):721–728), by Keogh et al. ("Albumin binding surfaces for biomaterials," J Lab Clin Med 1994 Oct;

124(4):537–545), and the like. The disclosure of each of these publications is hereby incorporated by reference into this specification.

In one embodiment, the biologically active material is coated onto a relatively smooth section 312 and/or 320 in order to form the roughened surface. As will be apparent, either the roughed surface, and/or the coated surface, will tend to promote adhesion between the implant assembly and the biological tissue surrounding it.

One means of facilitating such adhesion is to impart a charge to one or more of the implant surfaces. Thus, e.g., one may incorporate anions and/or cations into or onto such surface, as is disclosed in such U.S. Pat. No. 6,344,061. Thus, e.g., one may incorporate charged moieties into or onto such surface by the process disclosed in an article by P. S. Chockalinagm et al. entitled "DNA affinity chromatography," J. Mol Biotechnolgy 2001 Oct 19(2): 189–199.

In one embodiment, protein is coupled to silanized titanium with gluaraldehyde. See, e.g., the article by Wojcik et al., "Biochemical surface modification . . . ," Biomed Sci Instrum 1997; 33: 166–171.

Referring again to FIGS. 37A and 37B, and in the preferred embodiments depicted therein, it will be seen that head section 308 extends a distance 323 above the top surface 325 of ledge 322 of from about 2 to about 8 millimeters and, preferably, from about 2 to about 4 millimeters.

The implant assembly of this invention may be used in the process disclosed in U.S. Pat. No. 6,068,479 and, in particular, in the FIG. 18 depicted therein; the entire disclosure of such U.S. Pat. No. 6,048,479 is hereby incorporated by reference into this specification.

Thus, e.g., referring to such U.S. Pat. No. 6,048,479 and, in particular, to the FIG. 18 thereof, in the first step of this process, step 300, abutment 10 is connected to implant fixture 114.

In this step, it is preferred to apply a torque no greater than about 20 Newton/centimeter.

Thereafter, in step 302 of the process, a hole is drilled in the jawbone of the patient sufficiently deep to receive only the length of the implant fixture. In general, this hole is usually from about 8 to about 18 millimeters.

Thereafter, in step 304 of the process, the hole thus drilled is preferably tapped with a tapping tool such as, e.g., the screw taps illustrated on page 11 of the Nobelpharma catalog.

Thereafter, in step 306 of the process, the abutment/implant fixture assembly is delivered to the hole by means of the carrier 90. The carrier 90 may also be used to start screwing the assembly into the hole, applying downward pressure while turning the assembly.

Generally, the carrier 90 will only enable one to drive the abutment/implant fixture assembly a portion of the required distance. The job may be finished by a power-driven socket wrench in step 308 of the process.

In the next step of this preferred process, step 310, the healing ball 160 is preferably snapped onto the abutment 10. In one preferred embodiment, the healing ball 160 is disposed within compartment 101 of carrier 90 prior to its use.

Thereafter, in step 312, the gum tissue where the hole had been drilled is sutured around the healing ball 160.

In the next step of process, step 314, the surgical site is allowed to heal before the abutment 10 is directly or indirectly connected to a denture. In general, a healing period of from about 3 to about 6 months is desirable.

After the desired time of healing, no additional surgical procedure is required, unlike the prior art process (which necessitated second stage surgery to remove the cover screw used in the process and to attach the prosthetic abutment). By comparison with prior art processes, applicant's prosthetic abutment is already attached.

At this stage of applicant's process, several options are available. In one embodiment, illustrated in step 316 of U.S. Pat. No. 6,068,479, the healing ball is attached directly to a denture into which metal caps with an O-ring have been cured.

In another embodiment, illustrated in step 318, the healing ball 160 is removed from the abutment 10. At this stage, several additional options are available.

One such option is to attach the gold cylinder 190 on the abutment 10 in step 320. Once the gold cylinder 190 has been so attached, one may prepare a bar clip overdenture (see FIG. 12) and attach such denture to the superstructure (see step 322). Alternatively, in step 324, the gold cylinders 190 can be incorporated into a fixed detachable implant supported bridge and thereafter secured to multiple implants in place in the jawbone.

Alternatively, in step 326, after the healing ball 160 has been removed a gold coping 210 may be attached to a tooth where such a gold coping is imbedded in the tooth). Thereafter, in step 328, such tooth is attached to the abutment 10.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

We claim:

1. A dental implant assembly comprised of an integral dental implant, wherein said integral dental implant is comprised of an abutment head an implant body, and a neck section comprised of a ledge, wherein said ledge section is disposed between, and integrally joined with, said abutment head and said implant body wherein:
   (a) said abutment head is comprised of top section and a bottom section integrally joined to said top section, wherein:
      i. said top section has a shape formed by a linear wall adjacent to an arcuate wall,
      ii. said abutment head has a length of from about 2 to about 4 millimeters
      iii. said bottom section is integrally joined to said neck section;
   (b) said implant body is comprised of a top section and a bottom section, wherein said implant body extends upwardly and outwardly from said bottom section to said top section wherein said top section is integrally joined to said neck section;
   wherein:
      i. said implant body has a length of from about 3 to about 20 millimeters, and the surface of said implant body has an average irregular roughness of from about 10 to about 1,000 microns,
      ii. said neck section has a length of from about 0.1 to about 2 millimeters, and the surface of said neck section has an average roughness of from 0.1 to about 100 microns,
      iii. said length of said neck section is less than about 15 percent than said length of said implant body, and
      iv. said average irregular roughness of said implant body is at least about 10 times as great as said average roughness of said neck section.

2. The dental implant assembly as recited in claim 1, wherein said abutment head is comprised of an orifice extending through a portion of said top section of said abutment head.

3. The dental implant assembly as recited in claim 2, wherein said top section of said abutment head has a cross-sectional shape substantially like a polygon.

4. The dental implant assembly as recited in claim 3, wherein said ledge is a horizontally-extending ledge.

5. The dental implant assembly as recited in claim 4, wherein said abutment head is comprised of a base which extends upwardly and outwardly from its bottom to its top.

6. The dental implant assembly as recited in claim 1, wherein said abutment head is formed by a multiplicity of walls which are integrally connected to said ledge.

7. The dental implant assembly as recited in claim 6, wherein said multiplicity of walls is comprised of a first wall that it is substantially perpendicular to said ledge.

8. The dental implant assembly as recited in claim 7, wherein said multiplicity of walls is comprised of a second wall that is substantially perpendicular to said ledge.

9. The dental implant assembly as recited in claim 8, wherein said multiplicity of walls is comprised of a third wall that forms an acute angle with said ledge.

10. The dental implant assembly as recited in claim 9, wherein said acute angle is less than about 75 degrees.

11. The dental implant assembly as recited in claim 6, wherein said multiplicity of walls is comprised of a wall that forms an acute angle with said ledge.

12. The dental implant assembly as recited in claim 11, wherein said wall that forms an acute angle with said ledge is a linear wall.

13. The dental implant assembly as recited in claim 12, wherein said linear wall is integrally connected an arcuate wall.

14. The dental implant assembly as recited in claim 13, wherein said arcuate wall is comprised of a multiplicity of splines which have a substantially rectangular cross-sectional shape.

15. The dental implant assembly as recited in claim 1, wherein said implant body is comprised of a bioactive coating.

16. The dental implant assembly as recited in claim 15, wherein said bioactive coating has a thickness of from about 50 nanometers to 200 microns.

17. The dental implant assembly as recited in claim 16, wherein said bioactive coating has a thickness of from about 1 to about 50 microns.

18. A dental implant assembly comprised of an integral dental implant, wherein said integral dental implant is comprised of an abutment head an implant body, and a ledge section comprised of a ledge, wherein said ledge section is disposed between, and integrally joined with, said abutment head and said implant body wherein:

(a) said abutment head is comprised of top section and a bottom section integrally joined to said top section, wherein:

i. said top section has a shape formed by a linear wall adjacent to an arcuate wall, ii. said abutment head has a length of from about 2 to about 4 millimeters (b) said implant body is comprised of a top section and a bottom section, wherein said implant body extends upwardly and outwardly from said bottom section to said top section and said implant body has an irregularly etched surface such that said etched surface has an average irregular roughness of from about 10 to about 1,000 microns; and (c) said abutment head is comprised of a first wall that it is substantially perpendicular to said ledge, forming an angle of from about 75 to about 95 therewith, and a second wall that forms an angle with said ledge, wherein said angle is less than about 75 degrees.

19. The dental implant assembly as recited in claim 18, wherein said first wall is an arcuate wall.

20. The dental implant assembly as recited in claim 19, wherein said second wall is connected to a third arcuate wall, wherein said third arcuate wall is substantially perpendicular to said ledge, forming an angle of from about 75 to about 95 degrees therewith.

21. The dental implant assembly as recited in claim 20, wherein an orifice extends through a portion of said top section of said abutment head.

* * * * *